United States Patent
Sullivan et al.

(10) Patent No.: US 7,169,303 B2
(45) Date of Patent: Jan. 30, 2007

(54) SORBENT REACTOR FOR EXTRACORPOREAL BLOOD TREATMENT SYSTEMS, PERITONEAL DIALYSIS SYSTEMS, AND OTHER BODY FLUID TREATMENT SYSTEMS

(75) Inventors: Thomas A. Sullivan, Pine Village, IN (US); David J. Carr, West Lafayette, IN (US); Stephen R. Ash, Lafayette, IN (US)

(73) Assignee: HemoCleanse Technologies, LLC, Lafayette, IN (US)

( * ) Notice: Subject to any disclaimer, the term of this patent is extended or adjusted under 35 U.S.C. 154(b) by 0 days.

(21) Appl. No.: 10/856,540

(22) Filed: May 28, 2004

(65) Prior Publication Data

US 2005/0006296 A1    Jan. 13, 2005

Related U.S. Application Data

(60) Provisional application No. 60/473,896, filed on May 28, 2003.

(51) Int. Cl.
*B01D 63/06* (2006.01)
*B01D 61/28* (2006.01)
*B01D 24/36* (2006.01)
*B01D 29/86* (2006.01)
*B01D 63/00* (2006.01)
*B01D 61/00* (2006.01)
*B01D 29/00* (2006.01)

(52) U.S. Cl. .............. 210/321.63; 210/646; 210/512.3; 210/208; 210/206; 210/270; 210/271; 210/276; 210/280; 210/319; 210/332; 210/298; 210/305; 210/308; 210/320; 210/383; 422/44; 422/101

(58) Field of Classification Search ........... 210/321.63, 210/321.78, 321.87, 512.1, 512.3, 646, 226, 210/159, 208, 270, 271, 276, 280, 319, 332, 210/407, 297, 298, 305, 308, 309, 320, 383; 435/297.1, 297
See application file for complete search history.

(56) References Cited

U.S. PATENT DOCUMENTS 4,022,691 A * 5/1977 Heinrich .................... 210/202
(Continued)

FOREIGN PATENT DOCUMENTS

| JP | 63126509 A | * 5/1988 |
|---|---|---|
| WO | WO 93/15825 | 8/1993 |
| WO | WO 02/30267 | 4/2002 |

OTHER PUBLICATIONS

Mitzner, Steffen R. et al., "Albumin dialysis using the molecular adsorbent recirculating system", *Nephrology and Hypertension* 2001, 10:000-000, © 2001 Lippincott Williams & Wilkins.
(Continued)

*Primary Examiner*—Krishnan S. Menon
(74) *Attorney, Agent, or Firm*—Krieg DeVault LLP

(57) ABSTRACT

Systems and methods for extracorporeal processing of blood or other body fluid for the treatment of conditions, such as sepsis, autoimmune disease, or toxemia related to kidney failure, liver failure, or drug overdose are provided. In an extracorporeal treatment system, a fraction of a body fluid is passed into a treatment fluid, at least a portion of which is then passed through a sorbent suspension reactor for treatment by a sorbent suspension. The treatment fluid circuit can be maintained at a fixed volume, which enables accurate fluid balance between the patient and the extracorporeal circuit. Some or all of the treatment fluid, optionally also containing nutrients and/or therapeutic agents, is returned to the patient. In a peritoneal dialysis system, dialysate is passed into a patient's peritoneal cavity, recovered from the cavity, passed through a sorbent suspension reactor in accordance with the invention, and returned to the cavity.

46 Claims, 17 Drawing Sheets

U.S. PATENT DOCUMENTS

| | | |
|---|---|---|
| 4,350,156 A | 9/1982 | Malchesky et al. |
| 5,211,850 A | 5/1993 | Shettigar et al. |
| 5,538,630 A * | 7/1996 | Burns .................... 210/198.1 |
| 5,858,238 A | 1/1999 | McRea et al. |
| 5,925,246 A * | 7/1999 | Lee et al. .............. 210/321.68 |
| 5,980,479 A | 11/1999 | Kutushov |
| 6,059,970 A * | 5/2000 | Kohlheb et al. ......... 210/321.6 |

OTHER PUBLICATIONS

Sefer, Sinisa et al., "Artificial Liver: Present or Future?", *Acta Clin Croat* 2002; 41:245-254.

* cited by examiner

SORBENT REACTOR FOR EXTRACORPOREAL BLOOD TREATMENT SYSTEMS, PERITONEAL DIALYSIS SYSTEMS, AND OTHER BODY FLUID TREATMENT SYSTEMS

CROSS-REFERENCE TO RELATED APPLICATION

The present application claims the benefit of U.S. Provisional Application Ser. No. 60/473,896 filed on May 28, 2003, which is hereby incorporated by reference in its entirety.

BACKGROUND OF THE INVENTION

The present invention relates generally to devices and methods for extracorporeal treatment of body fluids, such as extracorporeal treatment of blood, to remove toxins and restore physiological balance. The invention also relates in other aspects to devices and methods for performing peritoneal dialysis.

Extracorporeal blood treatment has been used to remove toxins in several therapeutic settings including drug overdose, autoimmune diseases, kidney insufficiency or failure, and liver insufficiency or failure. The treatment can include withdrawing blood from the patient and passing the blood through a purification system. Examples of such systems include hemodialysis, hemofiltration, hemoperfusion, and plasmapheresis systems.

Some blood treatment therapies rely on the efficacy of sorbents. One example of a system that uses sorbents is the BioLogic-DT System ("the DT System"). The DT System includes a flat plate dialyzer that has a semi-permeable membrane. A sorbent suspension containing powdered charcoal and various ion exchangers is passed in contact with the dialysate side of the dialyzer membrane, and blood is passed in contact with the opposite side of the membrane. The sorbents can also be pre-equilibrated with a variety of additional or replacement nutrients and beneficial components that can cross the membrane to the blood stream. A portion of blood, including toxins and other blood components such as nutrients and electrolytes, can be transported across the membrane by diffusion and convection. Sorbents come into contact with and bind certain of these components in the dialysate. Toxins can be bound by the sorbents, while many nutrients and electrolytes are not bound. The non-bound components are transported back across the membrane to the blood side. Blood treated in the dialyzer then returns to the patient. The DT System uses alternating vacuum and pressure in the dialysate to move the dialyzer membranes, thus changing the volume of the blood-side circuit. This, in combination with control of valves in the blood side circuit, results in the unidirectional flow of blood through the blood-side circuit. The membrane motion also actively mixes the sorbent suspension at the membrane surface, reducing stagnation, and chemical saturation of the sorbents by toxins at the membrane surface. Sorbent suspension also circulates between a reservoir and the dialyzer.

Another approach is the use of a sorbent suspension to treat blood components extracted from whole blood via plasma filtration. One example of this approach is the BioLogic-PF System ("the PF System"). In the PF System, blood is perfused through a hollow-fiber plasmafilter, and the transmembrane pressure is alternated from positive to negative on a regular cycle. In each cycle, about 40 ml of filtrate (plasma) is drawn out of the blood through the membranes, treated, and then returned to the blood, about 5 times per minute. Outside the membranes is a sorbent suspension containing charcoal or other powdered sorbent. The sorbent is also circulated between a reservoir and the case surrounding the hollow fiber membranes. Contact of the filtrate with the sorbent suspension removes soluble and protein-bound toxins from the filtrate. The filtrate then returns to the blood depleted of these toxins. Similar to the DT System, the sorbent has low capacity and affinity for many nutrients and can even supply nutrients by desorption. The back and forth motion of the filtrate reduces stagnation and chemical saturation of the sorbents on the outside of the plasma filter membranes and also avoids excessive red cell polarization on the blood side of the membranes.

Sorbents used in the DT and PF Systems have adequate capacity to remove toxins from blood and to restore a physiological balance; however, the presence of sorbent particles adjacent to dialysis or plasma filtration membranes gives rise to significant technical challenges, and often leads to mechanical obstructions. As a result, the use of a sorbent suspension adjacent to a separation membrane imposes severe limitations upon membrane choices and treatment system design. Furthermore, supplies of dialysis membranes suitable for such use in the DT System are limited, and it is expected that in the near future such membranes will not be commercially available. Recent advances in membrane technology have provided a variety of new membranes, such as, for example, highly efficient hollow fiber membranes; however, the challenges of passing a sorbent suspension in contact with such membranes have been a limiting factor in the overall success achieved in the use of a sorbent suspension in systems including such membranes.

In light of the above, there is a continuing need for improved systems for the treatment of body fluids in patients suffering from diseases and conditions such as drug overdose, autoimmune diseases, kidney insufficiency or failure, and liver insufficiency or failure. In particular, there is a need for systems that take advantage of new membrane technology, while also having the advantages provided by the use of sorbent suspensions. The present invention addresses these needs and provides additional benefits.

SUMMARY OF THE INVENTION

The present invention relates to an extracorporeal system for treating a body fluid or portion thereof. The system includes a Sorbent Suspension Reactor (SSR) that contains a sorbent suspension in a chamber through which a dialysate, filtrate, or other treatment fluid is passed to improve the physiological condition of the patient by removing toxins from the treatment fluid and, optionally, adding desirable materials. A sorbent suspension reactor in accordance with the invention can be readily used with existing therapy systems and can also be incorporated into new system designs. In addition, the versatility of the sorbent suspension reactor enables the use of an inventive reactor in combination with dialyzers or other separation membranes that best fit the therapeutic needs of a given patient. For example, the SSR can be used to treat either the dialysate in therapies similar to hemodialysis or plasma produced by any plasma separation method. While the invention is described primarily in terms of treating blood, it is to be understood that other body fluids, such as ascites fluid or peritoneal dialysate can also be treated in accordance with the invention. In many treatment protocols provided by the invention, such as, for example, plasmafiltration protocols, the treated fluid is returned to the patient. In other inventive protocols, such as, for example, hemodialysis protocols, the treatment fluid is not returned to a patient but is purified in the SSR so that it can be recycled through the dialysis instrument in contact with the separation membrane therein.

In one form, the present invention provides an extracorporeal treatment system that includes a treatment fluid circuit and a blood circuit. A treatment fluid passes through the treatment fluid circuit, which can include a sorbent reactor for treating the treatment fluid. Blood or other body fluid passes through the blood circuit. A separation membrane positioned between the blood circuit and the treatment fluid circuit allows selective migration of a portion of the fluids between the two circuits.

As used in this context, the term "treatment fluid" refers to a dialysate, a filtrate, or other fluid that contacts a side of a separation membrane opposite the side contacted by blood or other body fluid during an extracorporeal treatment. This can include any fluid in the treatment fluid circuit that can carry unwanted materials away from the blood or blood circuit. This term also refers in other contexts to a component of blood or other body fluid that is extracted from the blood or other body fluids using other separation means, passed through an inventive sorbent suspension reactor, and returned to the blood or other body fluid. In another aspect of the invention, this term also refers to a peritoneal dialysis fluid that passes through the peritoneal cavity of a patient, passes through an inventive sorbent suspension reactor, and then passes back into the patient's peritoneal cavity.

When a sorbent suspension reactor of the invention is used in combination with a dialyzer, most of the transfer of small molecules from blood to dialysate is by diffusion rather than convective flow. The treatment fluid in such a system contains small molecules and toxins in similar concentrations to those of a filtrate created by convection using the same membranes. In a plasma filter system, the treatment fluid can be completely derived by filtration from the blood. In another manner of separation of plasma from blood for passage through a treatment fluid circuit, a plasma centrifuge is used as the separation device.

In an extracorporeal treatment system, the treatment fluid is passed through the sorbent reactor at a location in the treatment fluid circuit that is remote from the separation membrane or other separation device. The reactor includes a housing having at least one filter for containing solid sorbent particles inside the reactor during operation as the treatment fluid flows therethrough. The filter within the reactor can have a wide variety of configurations, and the selection of a filter configuration can be based on the performance and practicalities of the various options. A rotor inside the reactor can facilitate homogeneous suspension of the solid particles in the reactor and can prevent polarization or accumulation of sorbent particles next to the filter, which would decrease the rate of treatment fluid flow. The rotor may also effect or assist transport of the treatment fluid through the filter.

In another form, the present invention provides an apparatus for extracorporeal treatment of a body fluid that includes means for separating components of interest from the body fluid into a treatment fluid. The apparatus also includes a reactor for treating the treatment fluid, means for conveying the treatment fluid to the reactor, and means for returning the treatment fluid back to the body fluids or to the patient. The means for separating can include a separation apparatus incorporating any number of biocompatible means for removing components from body fluid and which can be tailored for a specific treatment or therapy. Examples of biocompatible means include, but are not limited to, a membrane filtration device, a dialysis device, and a centrifugation device. The means for conveying the treatment fluid to the reactor can include an input to the reactor consisting of tubing, and/or biocompatible pumps, such as a peristaltic pump, a pump built into the reactor, and other known and widely used fluid pumping systems known in the relevant art. Similarly, the means for returning the treatment fluid back to the body fluids or to the patient can include tubing and biocompatible pumps as noted above.

The reactor can include one or more of: a treatment chamber for treating the treatment fluid; a sorbent suspension contained in the treatment chamber; one or more filters to contain the sorbent suspension within the treatment chamber; and one or more means for mixing the contents including the sorbent suspension, the treatment fluid, and/or any other added components, in the reactor. The reactor can also include a means for clearing the surface of the one or more filters, such as, for example, by means employing mechanical and/or hydraulic action. The one or more filters in the reactor can have one or more of the following features: the filters can be disposed on or about the periphery of the treatment chamber, the filters can contain certain contents within the treatment chamber, and the filters can be supported in such a manner as to allow free passage of appropriate treatment chamber components such as treatment fluids, nutrients, and/or added components.

The sorbent suspension for use in the reactor can have any one of the following features: the sorbent suspension can include a variety of solid particles to adsorb some contents of the reaction chamber, particularly, toxic components originating from the blood or the blood circuit; the sorbent particles can include beneficial materials to be released into the body fluid in the reaction chamber; the sorbent particles can exhibit a large surface area for high capacity adsorption or exchange within the treatment chamber contents; and the solid particles can be provided in a small particle size, typically less than 100 microns, more commonly, averaging less than 20 microns. Additionally, components that impart and/or maintain desirable physical and chemical properties can be added to the sorbent suspension.

The means for mixing the contents of the reactor can include any one or more of the following features: a rotating element that extends substantially the length of the chamber and a mechanism for imparting rotary motion to the rotating element, such as, without limitation, various electrical, mechanical, magnetic, and hydraulic drive systems. The rotating element can include blades or baffles positioned in close proximity to the filter. The mixing apparatus can generate forces to pump the chamber contents either into or out of the reaction chamber.

The extracorporeal treatment system for use in the present invention may have additional subsystems. One subsystem can include a mechanism for removing gases from the extracorporeal circuit. The degassing mechanism can include a chamber in line with the treatment circuit, a fluid level sensor, a vacuum port or source, and controller operatively coupled with the vacuum port or source. In this context, "vacuum port or source" can include a positive displacement pump or other pump to remove gas.

Another subsystem monitors the liquid volume and/or maintains a constant liquid volume in the extracorporeal circuit. This system can remove a pre-selected liquid volume from the circuit and thus from the patient. The desired volume can be pre-selected either prior to treatment or during treatment of a patient. The same pump can be used for the gas removal and liquid volume subsystems by monitoring the inlet fluid stream to the pump for the presence of either gas or liquid and adjusting the total volume pumped to attain the pre-selected fluid removal.

The liquid volume subsystem includes a means for evaluating or analyzing the treatment fluid composition, including electrolyte and/or toxin concentration. The fluid removed from the circuit can also be analyzed and then disposed of, if desired.

The system can also include a subsystem to add anticoagulants and/or to induce anticoagulation of the components contained in the extracorporeal circuit. The anticoagulation components and/or system can include any one of the following: adding an anticoagulant to the body fluid, measuring the anticoagulation properties of the body fluid or treatment fluid, adding one or more antagonists to anticoagulation to the body fluid returning to the patient to restore the fluid to a desired physiological condition, and/or including a feedback control or reading of the anticoagulant and its antagonist based on the measurements of appropriate fluids.

For example, the extracorporeal circuit may be kept anticoagulated by regional administration of citrate. The calcium content of the blood coming out of the patient will be monitored by an ion-selective electrode or other similar technology. Citrate will then be added to the blood. The calcium content of the fluid that is of most interest for anticoagulation will be measured. The citrate dose will be regulated to keep this concentration in the proper range. Calcium will be added to the treated blood just before it is returned to the patient. The calcium dose will be regulated to keep the blood in the desired range.

In yet another form, the present invention provides an apparatus and method for maintaining the fluidity of the sorbent suspension and avoiding clogging of the filter in the reactor. One approach is to place a blade or baffle of a rotor in close apposition to the filter and to rotate the rotor to scrape or to provide shear or other hydraulic action that lifts sorbent particles from the filter surface. Another approach is to intermittently reduce or stop outflow, thereby reducing or zeroing pressure across the filter, allowing the rotor to lift sorbent particles off the filter. Such a procedure can also optionally include forcing some fluid backwards across the filter to lift particles from the surface. Still yet another approach is to shunt the sorbent suspension from the perimeter (or circumference) of the reactor to flow across the surface of the filter in a direction parallel to the axis of the rotor to an end of the reactor, and then back toward the center, i.e., axis, of the reactor chamber. This, in effect, attenuates or short-circuits the centrifuge effect of a rotating rotor or mixer. This procedure can include providing additional shunt chambers within the interior of the reactor.

In another aspect of the invention, the sorbent system reactor can be used in a treatment fluid circuit configured for use in a continuous flow-through peritoneal dialysis system. In such a system, the patient's peritoneal membrane is the separation membrane of the system, and the treatment fluid circuit includes the patient's peritoneal cavity, the sorbent suspension reactor, and conduits and treatment fluid pumps for passing the treatment fluid therebetween.

Other aspects of the invention include methods for conditioning a treatment fluid that passes in contact with a separation membrane, or that is otherwise separated from blood or other body fluid, by passing the treatment fluid through a sorbent suspension reactor made or selected in accordance with the present invention.

Further objects, features, aspects, forms, advantages, and benefits shall become apparent from the description and drawings contained herein.

DETAILED DESCRIPTION OF THE INVENTION

For the purposes of promoting an understanding of the principles of the invention, reference will now be made to the embodiments illustrated herein, and specific language will be used to describe the same. It will nevertheless be understood that no limitation of the scope of the invention is thereby intended. Any alterations and further modifications in the described processes, systems, or devices, and any further applications of the principles of the invention as described herein, are contemplated as would normally occur to one skilled in the art to which the invention relates.

Figure 1:
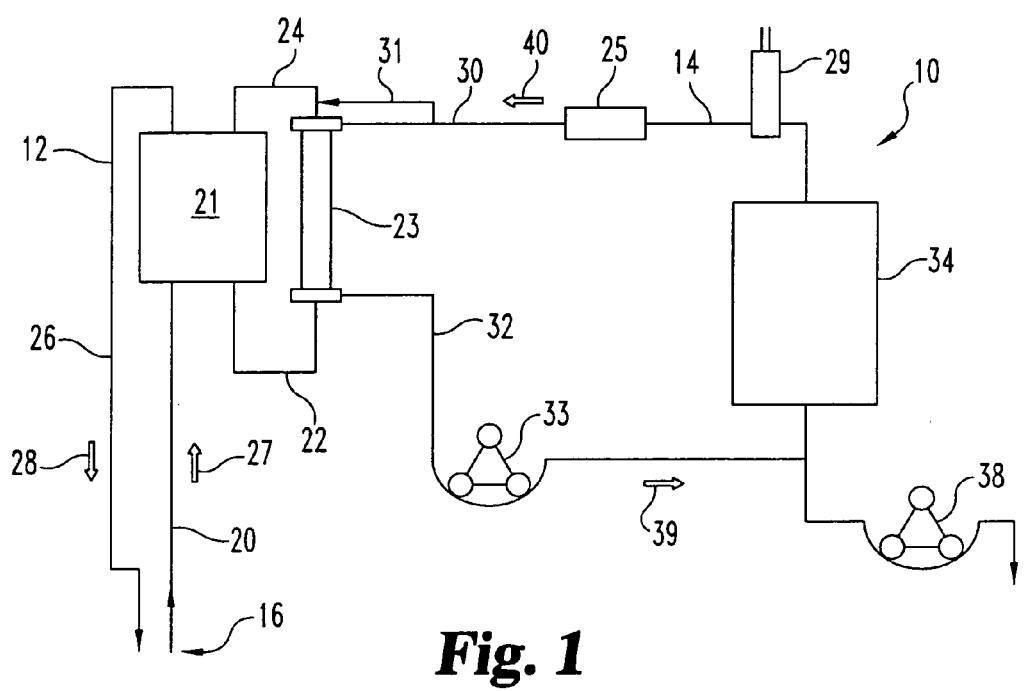
FIG. 1 is a schematic illustration of one embodiment of a sorbent suspension reactor system in accordance with the present invention.

FIG. 1 is a schematic illustration of an extracorporeal system 10 in accordance with the present invention. System 10 is composed of a blood circuit 12 and 22 and a treatment fluid circuit 14. A treatment fluid flows through circuit 14. If desired, the treatment fluid can contain beneficial additives that can be transferred to the blood. Typically, the treatment fluid can include any fluid that is physiologically acceptable and compatible with blood. In a preferred embodiment, the treatment fluid is substantially free of particles. During actual treatment, the treatment fluid can include plasma or other components of the patient's blood, depending upon the pore size of the separation membrane (not shown) of separation device 23. In other embodiments, the treatment fluid is composed substantially of a component of the patient's blood that has perfused through the separation membrane described below more fully. In this embodiment, the treatment fluid can include a component of fluid that was prepared and used to initially prime the extracorporeal system. In the treatment fluid circuit 14 illustrated in FIG. 1, a substantially continuous recirculation of the treatment fluid during operation is contemplated.

Access to the vascular system of a patient in need of treatment can be achieved either through a single-lumen or a dual-lumen access illustrated generally as 16. From the site of access 16, a blood inflow line 20 extends to pumping device 21. Pumping device 21 can be any commonly used or known device compatible with the blood and/or body, for example, a centrifugal pump or a peristaltic pump commonly used and known in the medical arts. The pumping device 21 propels blood through line 22 to separation device 23, where it passes in contact with a separation membrane (not shown). In one preferred embodiment, separation device 23 is a hollow fiber membrane configured to allow blood to flow through the interior of the fibers. Typically, a dialysate fluid or other treatment fluid surrounds the exterior of the fibers, depending upon the type of treatment being performed, as discussed more fully below. Blood exits separation device 23 into line 24, and it is returned to the patient. In the illustrated embodiment, blood flows through line 24 back through a pump. The pump can be the same pumping device 21, a different pumping device, or no pump at all. The blood is then returned through access 16 to the patient through infusion line 26. Blood circulates through blood circuit 12 in the direction indicated by arrows 27 and 28.

As above noted, a separation membrane (not shown) in separation device 23, which is typically a semi-permeable membrane, separates the treatment fluid from the blood. In some preferred embodiments, the treatment fluid flows countercurrent to the blood flow through separation device 23. After passing though separation device 23, the treatment fluid and any entrained toxins or other components flow through line 32 via pump 33 to sorbent reactor 34. Pump 33 is schematically represented as a peristaltic pump, but pump 33 may be any device capable of transporting fluid. After passage through sorbent reactor 34, treatment fluid passes through line 30 of treatment fluid circuit 14 through an optional degasser 29 and then to separation device 23, where it contacts the separation membrane. An optional or alternate return line 31 is also indicated in FIG. 1. Alternate return line 31, which finds advantageous use in plasmafiltration devices, returns fluid from reactor 34 directly into line 24, i.e., the blood return line. In the embodiment shown in FIG. 1, treatment fluid circuit 14 also incorporates a heater 25 that warms the treatment fluid prior to its return to line 24 or to separation device 23, thereby reducing the chance that the patient will suffer discomfort or become chilled due to reintroduction of blood that is below body temperature. It is, of course, understood that heater 25 is optional and can be omitted in other embodiments of the invention.

With respect to separation device 23, many suitable separation systems are known for use in blood or other filtration applications, and those skilled in the relevant art will be readily able to select and utilize suitable separation membranes in the present invention. Three major groups of blood separation applications are hemodialysis, hemofiltration, and plasma separation. Each of these has specific implications for the selection of the separation membrane and the design of the system that uses them.

Hemofiltration membranes can be, for example, cellulosic membranes (e.g. cellulose acetates), polyethylene, or polyethersulfone (PES) membranes having molecular weight cutoffs of about 50,000. Suitable hemofiltration membranes include those known under the designations F-80 (50,000 MW cutoff, Fresenius USA, Inc., Walnut Creek, Calif.), Altrex 140 (70,000 MW cutoff, Althin Medical, Inc., Miami Lakes, Fla.), and CT190G (60,000 MW cutoff, Baxter, Deerfield, Ill.). Preferred hemofiltration membranes will have pore sizes, which transmit albumin or middle molecular weight molecules with selectivity over larger molecules, and thus will provide removal of toxins while minimizing potential interference with other blood functions.

Suitable plasmafiltration devices include Plasmaflow AP-05H (L) (about 1,000,000 MW cutoff, Asahi Medical Co., Ltd., Tokyo, Japan). These have pore sizes sufficiently large to allow passage of plasma proteins. For example, the Plasmaflow AP-05H (L) plasma separator has about a 5% rejection of albumin during unidirectional filtration but about an 80% rejection of macroglobulins.

Turning now to dialysis systems, many dialyzer membranes are known for use in dialyzing body fluids such as blood, and those skilled in the relevant art will be readily able to select and utilize a suitable membrane in the present invention. One suitable membrane is a cellulosic membrane, particularly one composed of regenerated cuproammonium cellulose (Cuprophan). Other suitable dialyzer materials include polyacrylonitrile, cellulose acetate, and polyethersulfone.

Sorbent reactor 34 includes a treatment chamber, passages for treatment fluid to enter the treatment chamber, a particle-rejecting filter, passage for treatment fluid that has traversed the filter to exit the reactor, and a sorbent suspension contained within the treatment chamber. The sorbent suspension can include ion exchange particles, charcoal, and other adsorbents or reactants. The treatment fluid flows into the reactor and intermixes with the sorbent suspension. The sorbent suspension is selected to adsorb, or otherwise react with, the toxins entrained in the treatment fluid. The filter is selected to allow the treatment fluid, minus at least a portion of the entrained toxins, to cross the filter, while filtering out the sorbent particles, thereby retaining the sorbent suspension in the sorbent reactor. The filtered treatment fluid may recirculate through separation device 23 in a direction indicated by arrows 39 and 40. Alternatively, as stated above, in certain hemofiltration or plasmafiltration protocols in accordance with the invention, the treatment fluid, which is primarily composed of a purified blood filtrate, may be added directly to the blood return line 24 via line 31.

Sorbent reactor 34 contains a sorbent suspension selected for the desired fluid treatment. A person skilled in the art will appreciate that the reactor system can be readily adapted to accommodate a wide variety of commercial blood treatment systems and treatment protocols. As such, sorbent reactor 34 is very versatile, and can be connected in-line in a wide variety of treatment fluid circuits with little or no modification, except perhaps selection of a particular sorbent composition indicated for a given type of treatment. Indeed, one significant advantage of the invention is that the sorbent suspension is held in a sorbent reactor remote from separation device 23, thus maintaining discreet locations for the separation process and the sorbent treatment. Examples of advantages provided by this orientation are provided in the following paragraphs.

First, separation of the separation process from the sorbent treatment location makes the system much more adaptable to a wide variety of separation processes and separation devices. In the current DT and PF Systems, the function of the entire system interacts in many ways with the performance of the dialyzer or plasmafilter, respectively. Attempting to change the filtration device would have a very large impact on system performance, and in the end, such change might not be possible without re-engineering the system. It is desirable, especially in DT-like applications, to be able to use dialyzers that are more biocompatible and have more desirable filtration characteristics. In plasma treatment systems like the PF System, the plasma can be produced by any suitable filter or even by alternative plasma separation technologies such as centrifugation.

Second, a sorbent reactor in accordance with the invention is more adaptable to changes in the sorbent. The sorbent reactor can be used with a wide variety of different sorbents or sorbent compositions. Further, the sorbent reactor can be provided as a modular unit that can be used as is or adapted for use with a particular extracorporeal treatment system and/or a particular sorbent composition. If necessary or desirable, separate reactors can be customized for each different type of sorbent composition, either in construction or operating conditions, without changing the whole extracorporeal treatment system.

Third, use of an inventive sorbent reactor allows more flexibility in the method of return of treated fluid to the patient. The sorbent function is not influenced by the means of returning the treated fluid to the patient, whether it is through dialyzer membranes in a system similar to the DT Systems or directly to the patient as would be possible with plasma treatment.

Fourth, interaction of the treatment fluid with the sorbent suspension can be controlled by the flow rate through the reactor and sorbent mixing to get the desired treatment. The present invention provides particular advantages over current systems including an increased contact time between the treatment fluid and the sorbent.

Fifth, in a preferred embodiment, the treatment fluid is a clear liquid. Consequently, detecting any leakage of blood into the treatment fluid can be readily determined using known spectrophotometric techniques. Additionally, in many embodiments of the invention, the sorbent is separated from the blood circuit by two barriers, i.e., the sorbent reactor filter and the separation membrane. This minimizes the risk that any sorbent will enter the blood circuit. However, should any leakage occur, either leakage of the sorbent into the treatment fluid or into the blood circuit, the presence of the leaked sorbent can also be readily detected by similar spectrophotometric techniques.

Sixth, one constant concern with current systems is preventing sorbents from becoming stagnant and ineffective in both the membrane separator and the sorbent reservoir. Various designs of an inventive reactor assure that the sorbent will be mixed and available to treat the treatment fluid.

Seventh, the present invention simplifies startup procedures, and, in particular, priming the system immediately prior to treating a patient. By separating the sorbent reactor from a separation device, many problems with priming a separation device with a sorbent suspension are avoided. When the sorbent suspension is in the reactor, priming a dialyzer is very similar to the procedure for standard hemodialysis. Specialized priming procedures required by the sorbent suspension are now confined to the reactor. It is expected that reactor priming procedures for many therapies will share many features.

In selected embodiments, it can be important to maintain a constant treatment fluid volume. This allows for volumetric control of the fluid balance for the patient. One manner of removing volume from the treatment fluid circuit and therefore from the patient (by net filtration across separation membrane of separation device 23) is also illustrated in FIG. 1. In this embodiment, treatment fluid can be removed from the circuit via pump 38. Pump 38 is schematically represented as a peristaltic pump, but pump 38 may be any device capable of transporting or releasing fluid to a point exterior to circuit 14. The removed fluid can be any excess fluid from the treatment fluid circuit and can include, but is not required to include, any of the components typically found in the treatment fluid. For example, a secondary semi-permeable membrane positioned upstream of pump 38 can be used to fractionate the treatment fluid, a portion of which can then be removed from the treatment fluid circuit via the pump 38. Such a system, for example, could remove water and salt from the treatment fluid circuit while leaving proteins in place in the circuit.

In embodiments of this invention with a fixed volume of circulating treatment fluid, the transfer across the separation membrane 23 will be both diffusive and convective. The convective component will be dependent upon the membrane porosity and pressure gradients in the system. For example, in a system in which the separation membrane is a hollow fiber membrane, the flow through the hollow fiber membrane necessitates that there is a pressure gradient between the inlet and outlet of the separation device. A similar phenomenon occurs in the treatment fluid side of the hollow fiber membrane. The pressure gradients along the length of the hollow fiber membrane in turn create transmembrane pressure gradients that vary along the length of the hollow fiber membrane. At one end of the hollow fiber membrane, i.e., the end that the blood enters, there is a mass transfer of filtrate from blood to treatment fluid. The mass transfer is reversed at the opposite end of the hollow fiber membrane, i.e., the end that the blood exits, where mass transfer from the treatment fluid to the blood occurs.

Figure 2:
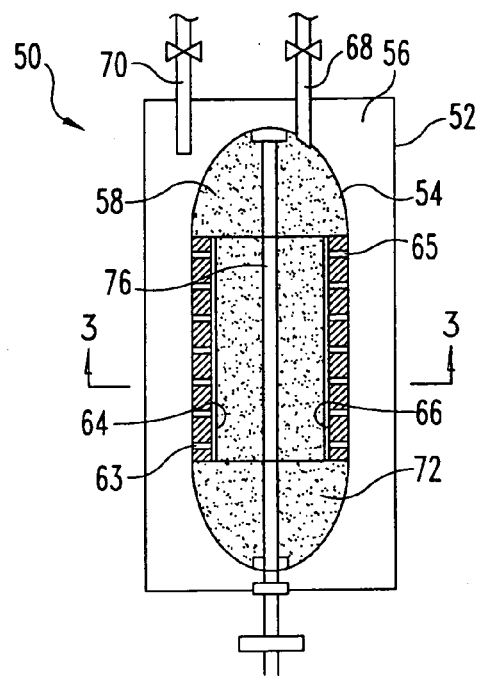
FIG. 2 is a cross-sectional view of one embodiment of a sorbent reactor for use in the extracorporeal treatment of blood in accordance with the present invention.
Figure 3:
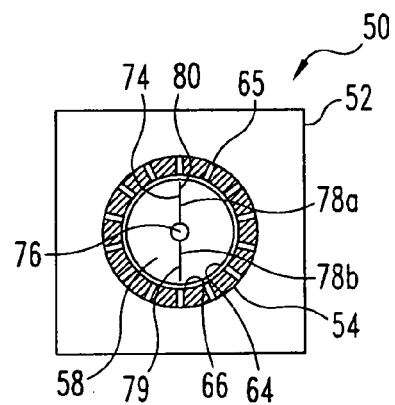
FIG. 3 is a cross-sectional view along section line 3—3 of the sorbent reactor illustrated in FIG. 2.
Figure 4:
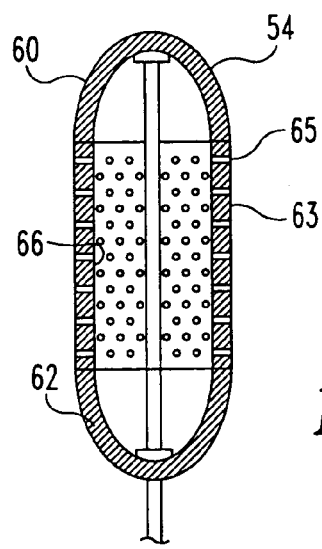
FIG. 4 is a cross-sectional view of the inner casing of the sorbent reactor illustrated in FIG. 2.

FIG. 2 illustrates a cross-sectional view of one embodiment of a sorbent reactor 50 for use in the present invention. Sorbent reactor 50 includes a reactor housing 52 and an inner casing 54. Inner casing 54 divides the sorbent reactor 50 into an outer region 56 and an inner region 58. During use of the reactor, a sorbent suspension 72 is present in the inner region 58. Inlet 68 provides fluid communication from the treatment fluid circuit to inner region 58. Outlet 70 provides fluid communication from outer region 56 back to the treatment fluid circuit. Thus, a treatment fluid entering inner region 58 through inlet 68 must pass from inner region 58 to outer region 56 before leaving reactor 50 through outlet 70. Referring additionally to FIGS. 3 and 4, inner casing 54 is provided as a substantially cylindrical casing having hemispherical end portions 60, 62, and a sidewall 63 disposed therebetween. Sidewall 63 is perforated with a plurality of openings 65 extending therethrough to allow treatment fluid flow therethrough. The hemispherical ends are optional and useful for some embodiments, whereas flat ends (creating a regular cylinder) or other configurations can be selected in other embodiments. It will be understood that a wide variety of other configurations are contemplated as being included within the scope of the present invention.

A filter 64 is disposed on the inside walls 66 of sidewall 63. Filter 64 can be any known and desirable filter material, such as membrane filters or frits. For example, filter 64 can be a membrane filter commonly used in laboratory work for fluid purification. Such membranes can be, for example, cellulosic membranes (e.g. cellulose acetates) or polyethersulfone (PES) membranes and will typically, when used with plasma filtration, have pore sizes sufficiently large to allow passage of plasma proteins suitably having molecular weight cutoffs of at least 500,000. An example believed suitable for this purpose is Pall Corporation's Supor membrane (catalog number SUP08500), a low protein binding polyethersulfone membrane used in filtration. (Pall Corporation: 25 Harbor Park Drive, Port Washington, N.Y. 11050). The selected membrane has a pore size sufficiently small to contain the suspension particles (i.e., filter 64 is selected to inhibit transfer of the solid particles in the sorbent suspension 72 from inner region 58 to outer region 56), while at the same time the pore size must be large enough to pass the treatment fluid at an acceptable flow rate and to allow passage of large molecules such as, for example, blood proteins, that may be present in the treatment fluid in some applications of the invention. Variance from these pore size parameters may result in filter clogging, removal of desirable components from the blood, and/or leakage of sorbent particles into the treatment fluid. In one embodiment, the filter features pore sizes of from about 0.1 micron to about 2.0 microns. In another embodiment, the pore sizes are from about 0.2 to about 1.5 microns. In yet another embodiment, the pore sizes are from about 0.2 to about 1.0 microns. A particularly preferred filter is one featuring a pore size of about 0.8 micron.

One significant challenge encountered when attempting to separate a fluid from fine sorbent particles (for example, particles having sizes of less than about 100 microns, by passage through a filter in a continuous-flow system is that the particles polarize or accumulate against the filter and clog the filter, resulting in reduced flow or stoppage of flow. The filtration is even more difficult when the fluid contains albumin or other plasma proteins. In inventive sorbent reactors, a shear force is created parallel to the membrane through movement of rotor elements adjacent the surface of the filter. In addition, the sorbent reactor is designed to operate at a controlled pressure drop and/or at a controlled flow rate.

Now referring specifically to the embodiment depicted in FIG. 3, which is a cross-sectional view of reactor 50 taken along section line 3—3, rotor 74 is positioned within inner region 58. Rotor 74 includes a shaft 76 and one or more paddles 78. In the illustrated embodiment, rotor 74 includes two oppositely extending paddles 78a and 78b. In other embodiments, three or more paddles can extend from shaft 76. Rotor 74 is rotatably disposed within inner region 58. In one embodiment, paddles 78a and 78b extend from shaft 76 toward filter 64 and do not touch the surface of the filter. In other embodiments, the edges 79 and 80 of one or more of the paddles come very close to, or touch the surface of filter 64. Rotation of shaft 76 and paddles 78a, 78b serves to maintain the solid component of the sorbent in a homogeneous suspension. Additionally, rotation of the paddles within the inner region 58 serves to inhibit and/or reduce build up of any of the solid sorbent on the surface of filter 64. Rotor 74, in this embodiment, provides a uniform sorbent agitation along the entire length of the inner region 58. This gives a constant extraction function for the treatment fluid. Additionally, the support of the rotor at the end portions 60 and 62 of the inner casing 54 does not interfere with the filtering function. The paddles 78a, 78b may be of varying geometries, including solid, or with perforations of any size to limit pumping action or to change the internal fluid flow dynamics. Likewise, the edge may be flat or angled to attain particular required hydraulic or mechanical scraping functions. In yet other embodiments, rotor 74 need not include a straight shaft, and in alternate embodiments, rotor 74 has a spiral configuration or other configuration suitable for use in accordance with the invention. If the particles in the sorbent suspension form a solid cake build-up on the surface of filter 64, the flow of treatment fluid through sorbent reactor 50 can be stopped or reduced while continuing rotation of the rotor to maintain agitation. This can provide an important clearing function for the filter surface during operation.

Sidewall 63 of the inner casing 54 provides support for filter 64 and yet allows transfer of the filtered treatment fluid from inner region 58 to outer region 56. This function may be embodied by perforations, grooves, or any suitable geometry that mechanically supports the filter (e.g., membrane) yet allows the passage of fluid through the filter.

In reactor 50 and other preferred embodiments, the cylindrical configuration of the inner casing provides a high ratio of filter surface area to reactor volume. This in turn keeps the fluid flux across the filter relatively low, reducing the driving force for sorbent clogging of the filter and consequently keeping the pressure gradient across the filter low. Furthermore, the filter is uniformly supported on the porous surface in the inner casing. This provides for efficient filter function in the reactor. Additionally, the hemispherical end portions 60, 62 allow uniform pressurization under the operating conditions. Such pressurization can be achieved, for example, by pumping a treatment fluid through inlet 68 into the inner region 58, and/or by the pumping action created by the rotation of the rotor assembly 76, 74, 78a, 78b.

In certain preferred embodiments of the invention, some portion(s) of the entire assembly illustrated in FIGS. 2, 3, and 4 may be constructed and assembled as a single-use disposable component, while other components are permanent components of the treatment system. For example, in one embodiment, sidewall 63 and filter 64 can form a disposable filtering component that is configured to be releasably engaged to hemispherical end portions 60, 62, which can be provided as permanent components of the assembly, to form inner casing 54. In another, preferred, embodiment, all components contacting treatment fluid are disposable, while the remaining components provide additional mechanical support and rotor drive. It is also contemplated that sidewall 63 and filter 64 can be formed as a single unit, and that sidewall 63 can be omitted entirely in embodiments including a filter that is itself sufficiently rigid to maintain structural integrity of the system.

Figure 5A:
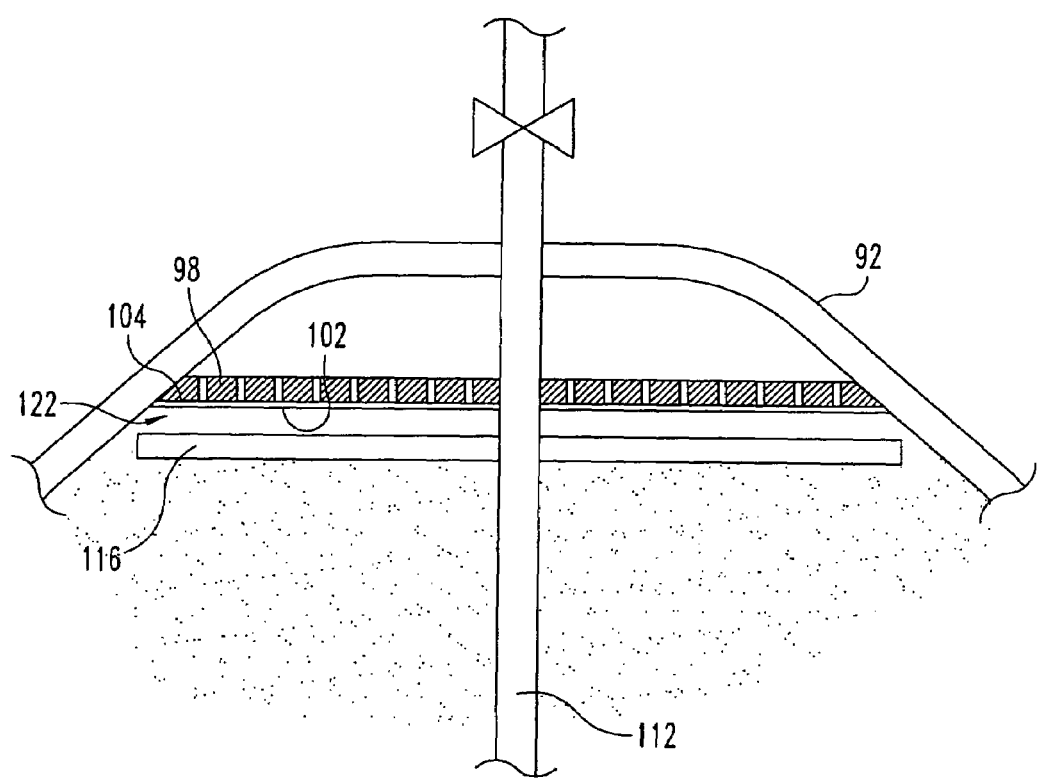
FIG. 5A is an enlarged cross-sectional partial view of the sorbent reactor illustrated in FIG. 5.
Figure 5:
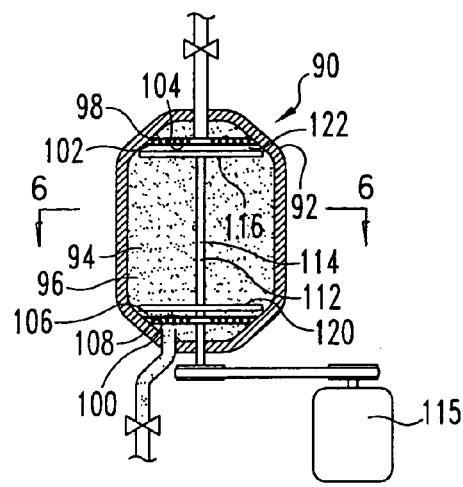
FIG. 5 is a cross-sectional view of an alternative embodiment of a sorbent reactor for use in the extracorporeal treatment of blood in accordance with the present invention.

FIG. 5 is a cross-sectional view of an alternative embodiment of a sorbent reactor 90 for use in the present invention. Sorbent reactor 90 includes a reactor housing 92 that defines an inner region 94 that can contain a sorbent suspension 96. Referring additionally to FIG. 5A, which is an enlarged partial view of the upper portion of sorbent reactor 90, housing 92 is illustrated as a generally cylindrical casing having a first filter support 98 and a second filter support 100. Supports 98 and 100 are provided as a substantially porous support to allow the treatment fluid to flow therethrough with little resistance. A filter 102 is positioned on an inner surface 104 of filter support 98. Similarly, a filter 106 is positioned on an inner surface 108 of support 100. It is also contemplated that supports 98, 100 and filters 102, 106 can be formed as a single unit, and that supports 98, 100 can be omitted in embodiments including a filter that is sufficiently rigid to maintain structural integrity of the system.

Figure 6:
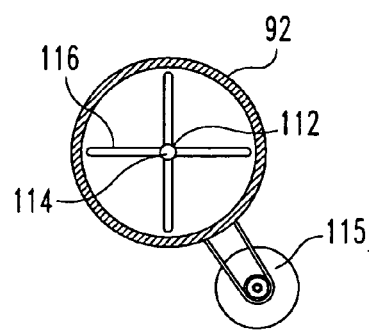
FIG. 6 is a cross-sectional view along section line 6—6 of the sorbent reactor illustrated in FIG. 5.

A rotor 112 is rotatably disposed within inner chamber 94. Referring now additionally to FIG. 6, which is a cross-sectional view of the sorbent reactor 90 taken along section line 6-6, rotor 112 is illustrated to include a shaft 114 having one or more blades 116. In the illustrated embodiment, rotor 112 includes two sets of blades 116 and 120. Blade 116 can be spaced apart from filter 102 by a gap illustrated by reference line 122. Rotation of shaft 114 rotates blades 116 creating a hydraulic force that can clear filter 102 from occlusion by the solid sorbent. In alternative embodiments, it will be understood that blades 116 can actually brush against filter 102. Lower blades 120 can be disposed within inner chamber 94 similar to blades 116. Additionally, while only two sets of blades 116 and 120 are illustrated, it will be understood that three or more blade sets can be vertically spaced on shaft 114. Additionally, blades 116, 120 may be of any required height and even may extend the length of shaft 114. The blades need not be uniformly long in the radial dimension along the length of the shaft. Additionally, each set of blades can have one, two, three, four, or more individual blades. Drive mechanism 115, which can be a motor or other drive mechanism, is coupled to the shaft 114 either directly or indirectly, for example, through a gear, belt, magnetic, pneumatic or wheeled drive system. Rotation of the rotor 112 within inner chamber 94 uniformly disperses a solid sorbent and limits accumulation of a sorbent on filters 102 and 106. Furthermore, in preferred embodiments, the treatment fluid flow can be stopped or reversed through the filters to clear any caked sorbent that may have accumulated thereon.

Figure 7A:
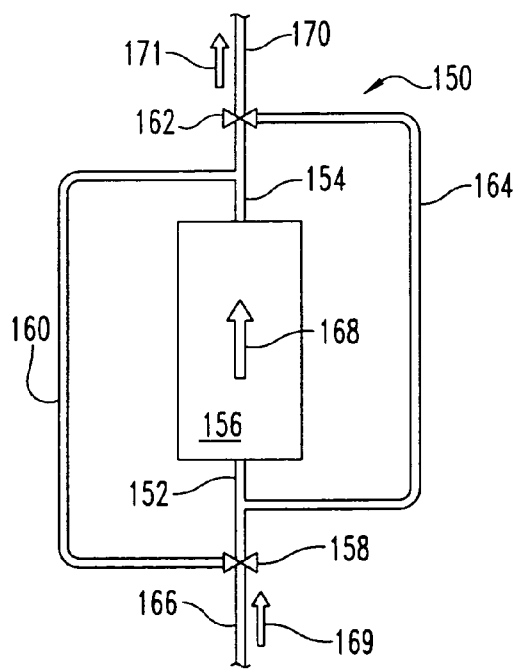
FIGS. 7A and 7B are diagrammatical illustrations, showing schematically, a method of reversing the flow through the sorbent reactor illustrated in FIGS. 5 and 6.
Figure 7B:
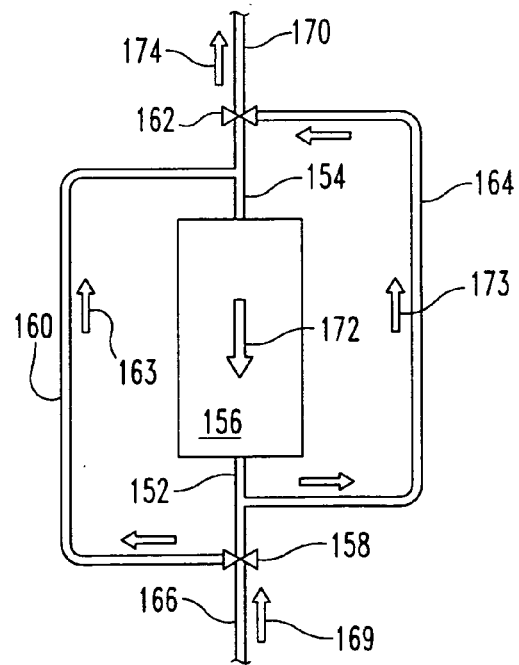

FIGS. 7A and 7B are diagrammatical illustrations depicting one embodiment of a procedure for reversing the flow through the reactor 90 illustrated in FIGS. 5, 6. Referring specifically to FIG. 7A, a portion of a treatment fluid circuit 150 is illustrated. The circuit portion 150 includes a first inlet 152 and a second inlet 154 leading into reactor 156. First inlet 152 includes a first bypass valve 158 and a first bypass line 160. Similarly, second inlet 154 includes a second bypass valve 162 and a bypass line 164. In preferred embodiments, bypass valves 158 and 162 are provided as three-way valves or as sets of tubing clamps, which alternately compress closed or release to enable fluid control in single use disposable tubing sets; a three way valve thus implemented would use two tubing clamps. In operation, treatment fluid flows through a first circuit line 166 in a direction illustrated by arrow 169. Treatment fluid continues through the first bypass valve 158 and first inlet 152 through reactor 156 in a direction depicted by arrow 168. The treatment fluid exits reactor 156 through second inlet 154 and bypass valve 162 and then flows through second circuit line 170 in a direction illustrated by arrow 171. In this embodiment, valves. 158 and 162 are adjusted so that treatment fluid does not flow through a first bypass line 160 or second bypass line 164.

Referring now specifically to FIG. 7B, first bypass valve 158 has been adjusted so that the treatment fluid flowing from first circuit line 166 is diverted to first bypass line 160, and second bypass valve 162 has been adjusted to direct flow from the second bypass line 164 to second circuit line 170. In first bypass line 160, the treatment fluid flows in a direction illustrated by arrow 163 through second inlet 154 and then through reactor 156 in a direction depicted by arrow 172. The treatment fluid then flows out through first inlet 152. Since first bypass valve 158 is a three-way valve, the treatment fluid cannot exit through first circuit line and is diverted through the second bypass line 164. In second bypass line 164, the treatment fluid then flows in a direction depicted by arrows 173 and 174 through second circuit line 170.

Reversing the flow of a treatment fluid through the reactor serves to force treatment fluid through a clogged filter, which in turn can clear the caked or clogged filter. The second encountered filter can then prevent any of the solid sorbent from entering the treatment fluid circuit. Alternatively, in a treatment system that is configured for only unidirectional flow through a sorbent reactor having a design similar to that shown in FIG. 5, it is to be understood that sorbent reactor can have only a single filter at the outlet end. For example, a filter in such a system would be positioned to separate the sorbent suspension from the outflow line; however, it is not necessary for the treatment fluid entering the sorbent reactor through inlet line to pass through a filter before contacting the sorbent suspension. The flow of the treatment fluid will prevent leakage of sorbent particles from the reactor. Such a system preferably includes means for ensuring that flow reversal does not occur. For example, a one-way valve could be included in the inflow line, or elsewhere in the treatment fluid circuit to prevent reversal of the fluid flow.

In certain preferred embodiments, a system includes an automated vacuum gas eliminator system, or degasser, to remove gas from the treatment fluid. Referring to FIG. 1, in one preferred embodiment, degasser 29 is positioned in the treatment circuit downstream of the SSR. However, it will be understood that the degasser can be positioned in other locations on the circuit.

Figure 24:
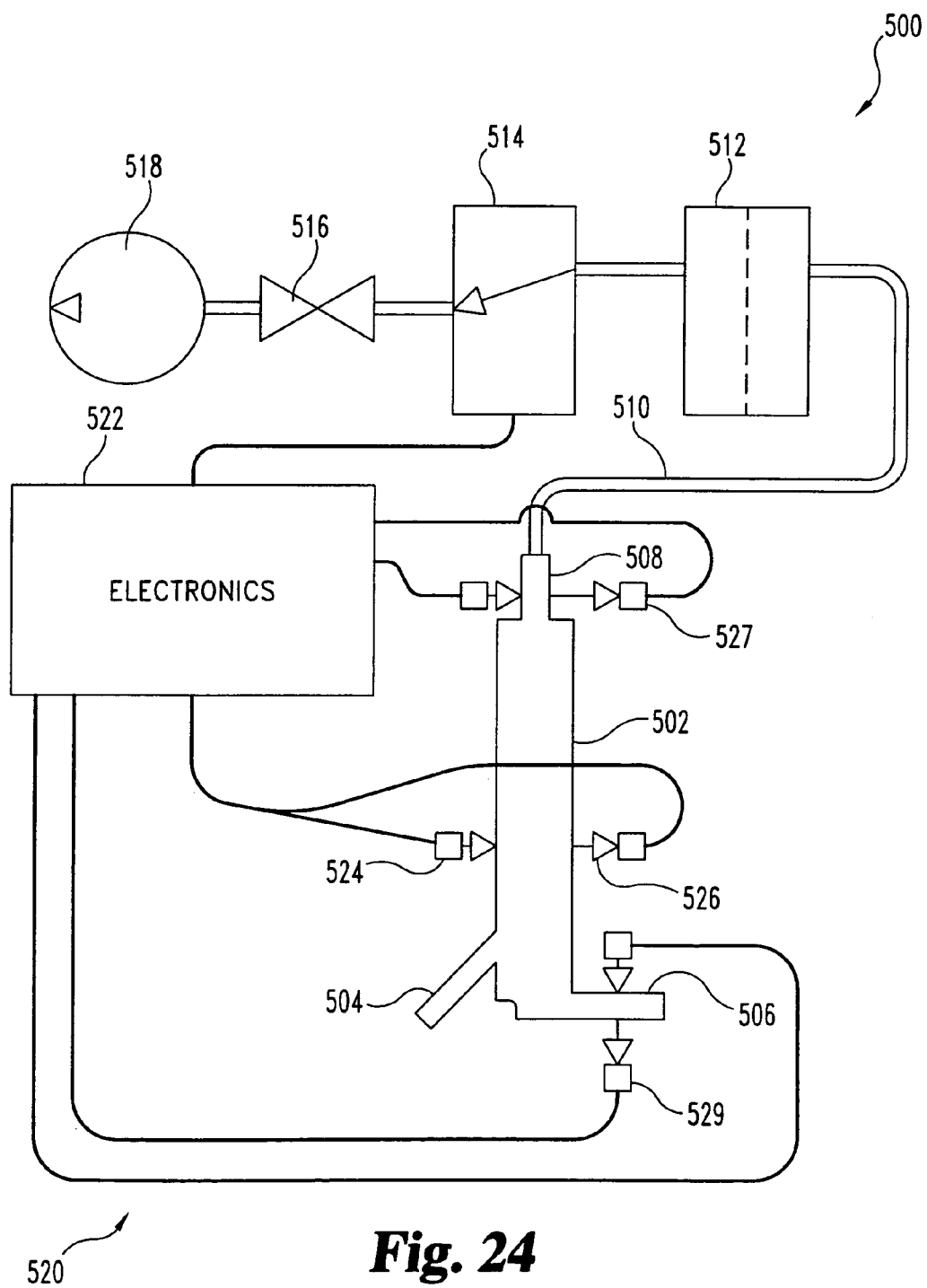
FIG. 24 is a schematic illustration of one embodiment of an automated vacuum gas eliminator system for use in the present invention.

FIG. 24 is a schematic illustration of one embodiment of an automated vacuum gas eliminator, or degasser, for use in the present invention. System 500 includes a column 502 having a liquid inlet 504, a liquid outlet 506, and a gas outlet or vacuum port 508 connected via vacuum line 510 to a source of vacuum or reduced pressure. It will be understood that while the term "liquid" is used to describe system 500, typically the liquid will be the treatment fluid for the extracorporeal fluid treatment system. Inlet 504 allows a liquid/gas mixture to enter column 502 at an angle. This provides for an efficient separation of the gas from the liquid as the gas continues to rise and the liquid falls to the bottom of column 502. The gas can then escape from the column through vacuum port 508. The degassed liquid can exit the bottom of the column through outlet 506. A vacuum takeoff is connected to vacuum port 508. The vacuum line 510 can include any of the following: a solenoid valve 514, a control valve orifice 516, and a vacuum pump 518 and optionally a filter 512 is preferably positioned upstream of these components (for configurations were only gas removed for column 502). Orifice 516 can also include a pressure and/or flow regulator or other suitable valve or control device. The source of vacuum can be created by a pump (typically positive displacement) or other suitable means, which pump or other means withdraws fluid from vacuum line 510 on demand in the same manner as described below with respect to solenoid valve 514.

The degasser also includes a detection system for detecting the level of liquid in column 502. In a preferred embodiment, the detection system includes an optical liquid level detector 520. The optical liquid detector 520 includes electronic control unit 522, light source 524, and sensor 526. In a preferred embodiment, light source 524 and sensor 526 are positioned such that the light exiting the light source does not pass through the center of column 502. In this configuration, clear fluid in the light path will refract the light beam away from the sensor, while turgid or opaque fluid will block light from the sensor. The system is thus rendered insensitive to the optical condition of the fluid. It will be understood, however, that other configurations, which will provide an adequate and accurate reading of the level of liquid within column 502, can be used in accordance with the present invention.

In operation, system 500 allows a mixture of liquid and gas to enter column 502 through entrance port 504. Inside column 502, gas separates from the liquid and rises to the top of column 502. The degassed liquid can then exit through port 506. The extracted gas can then be removed from column 502 through vacuum port 508. If the liquid level inside column 502 moves to a point below the optical path of optical liquid level detector 520, sensor 526 receives light from light source 524. In response, controller 522 opens solenoid valve 514, allowing the vacuum pump to extract gas from column 502 until the liquid inside column 502 rises to a predetermined level. In one embodiment, solenoid valve 514 remains open until the liquid inside column 502 reaches the level of the detector. The light emitted from light source 520 can then either be deflected or blocked so that it is not received by sensor 526. In either event, sensor 526 does not detect the light emitted from light source 524. In response, sensor 526 generates a signal that is received by controller 522, which in turn closes solenoid 514, thus shutting off or reducing the vacuum inside vacuum line 510 and column 502.

In another embodiment, an air/liquid sensor 527 is positioned adjacent port 508. Air/liquid sensor 527 is implemented in embodiments wherein components 518, 516, 514 and 512 are replaced with a fluid removal pump such as pump 38 in FIG. 1. By placing the fluid removal pump in this location, a single device can serve to extract both fluid and gas. This pump is typically a positive displacement type of pump such as a peristaltic pump. The pump is actuated at an appropriate flow rate, either on demand for fluid extraction, or in response to gas detection by detector 520. In contrast to the location of sensor 520 where the degasser tube 502 is wide and does not support permanent bubbles, port 508 is narrow and does support distinct bubbles or groups of bubbles with sufficient lifetimes to permit accurate determination of whether the fluid is substantially liquid or substantially gas. In such an embodiment, air/liquid sensor 527 enables the system to use the time during which gas is exiting through port 508, coupled with a known pump flow rate (for fluid removal pump 38 of FIG. 1, also 209 of FIG. 8), to calculate the actual volume of fluid. For example, if the pump is actuated by a system demand for fluid, the volume of gas detected by sensor 527 is subtracted from the total calculated fluid removal volume. If the pump is actuated by the demand of sensor 520, any liquid sensed by sensor 527 is added to the total calculated fluid removal volume.

Optionally a charcoal sensor 529 is positioned proximal to port 506. In a preferred embodiment, charcoal sensor 529 is an optical sensor and detector similar to that described above for sensor 526. In the illustrated embodiment, charcoal sensor 529 uses a straight-through optical beam. A continuous reduction in signal indicates the presence of charcoal in the liquid exiting port 506. An intermittent signal is indicative of small bubbles that may have escaped column 502. Additionally, as a backup, charcoal sensor 529 is also capable of detecting hemoglobin in the fluid exiting port 506, and consequently, can be used as a blood leak detector.

Gas eliminator system 500 provides particular advantages for systems that require or use a constant volume of treatment fluid. In operation, system 500 is shown to provide a gas removal efficiency of at least 99.88% and to provide an effluent from port 506 in which no gas bubbles were visible to the naked eye.

The embodiment of FIG. 1 also includes heater 25. In one preferred embodiment, heater 25 is an induction heater. It is to be understood, however, that other suitable heater technologies can be used in alternative embodiments. Induction heater 25 provides a desirable advantage in that its thermal transfer efficiency is high, while maintaining a high degree of patient safety from electrical shock. Other advantages of heater 25 include a modest disposable parts cost, quick heating ability enabling rapid start-up of system 10, mechanical ruggedness, and the ability to operate in a variety of positions and orientations.

Details of the construction and operation of heater 25 will now be described, with particular reference being made to FIG. 24.

In FIG. 24, heater 25 is shown as comprising a blood or treatment fluid heating loop 540, transformer element 542, and drive circuitry 544. Transformer 542 comprises a ferrite core 546, which may be of conventional design capable of operating in the range of 25 kHz to 40 kHz. While ferrite is the preferred embodiment, other materials exhibiting suitable magnetic characteristics may also be employed. Additionally, while the preferred range of operation is 25 KHz to 40 KHz, other frequencies may be acceptable and are within the scope of this application. Drive winding 548 forms the primary of transformer 542, while the secondary winding of transformer 542 is formed from loop 540. Loop 540 is illustratively constructed of 6 mm I.D.×7 mm O.D. stainless steel tubing. The tubing is shaped to form a substantially circular loop in order to maximize the transformer power factor, and hence efficiency of heater 25. The shape of loop 540 is preferably reasonably circular in order to reduce inductance in the secondary of transformer 542, yet allows adequate coupling to core 546 while minimizing EMI emissions. These advantages also allow a simplification of drive circuitry 544. Joint 550, which may be welded or brazed, completes the secondary side of transformer 542. In a practical application, primary winding 548 and any other electrical devices and components will be enclosed in a box or container (not shown) such that those components are not accessible to the patient. Line 552 in FIG. 24 represents the interface formed by the box or container structure. It is critical that there be no significant voltage presented to the tubing of loop 540. All electrical components, except a portion of core 546, are sealed under the top surface of the box or container. This permits easy cleaning while protecting the electrical components from fluid leaks. Heater 25 may also include a grounded electrostatic shield (not shown) to reduce EMI and prevent coupling of primary capacitance into the stainless steel tubing. Core 546 of transformer 542 is also grounded as it is typically attached to the electrostatic shield.

Figure 25:
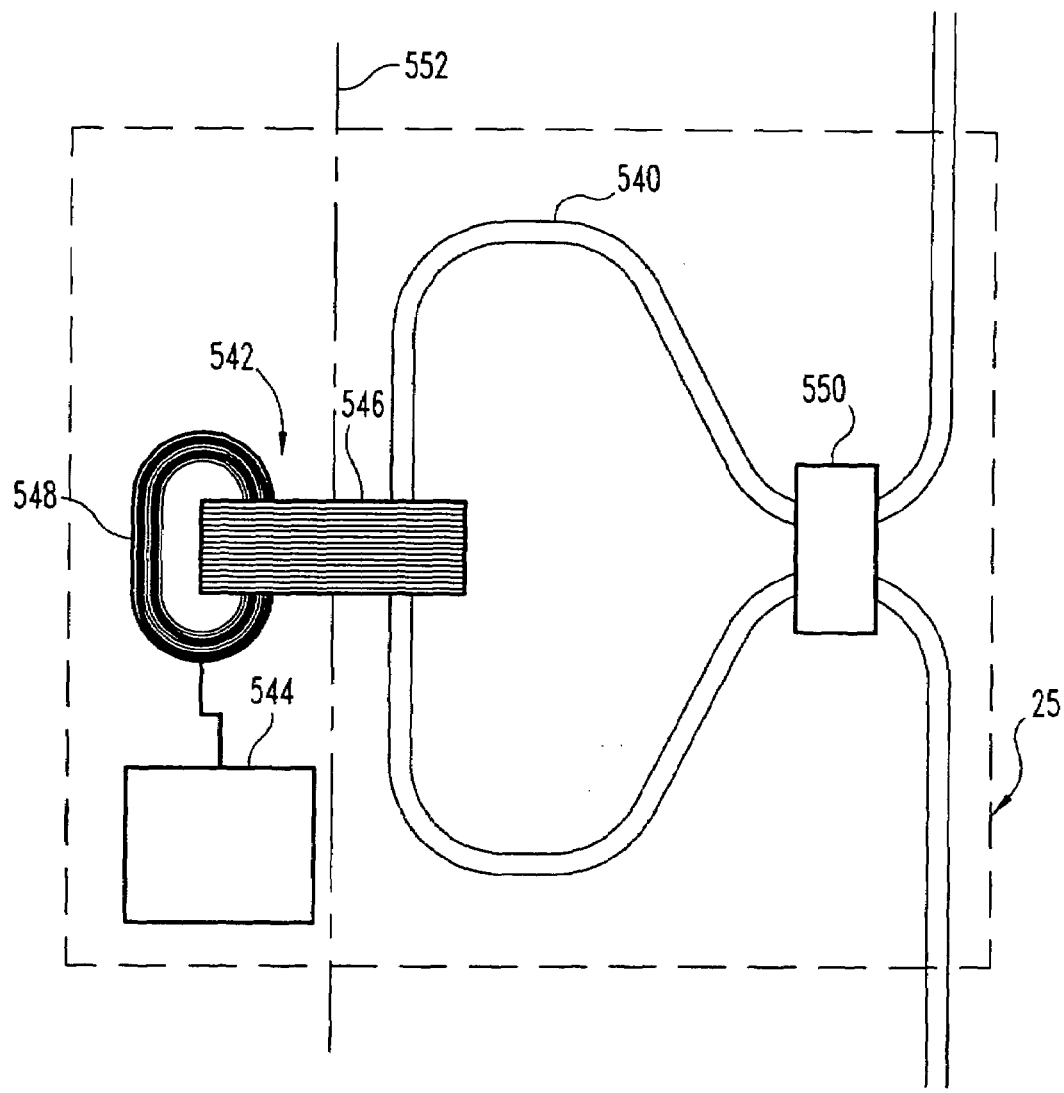
FIG. 25 is a schematic diagram of one embodiment of a dialysate heater for use in the present invention.
Figure 26:
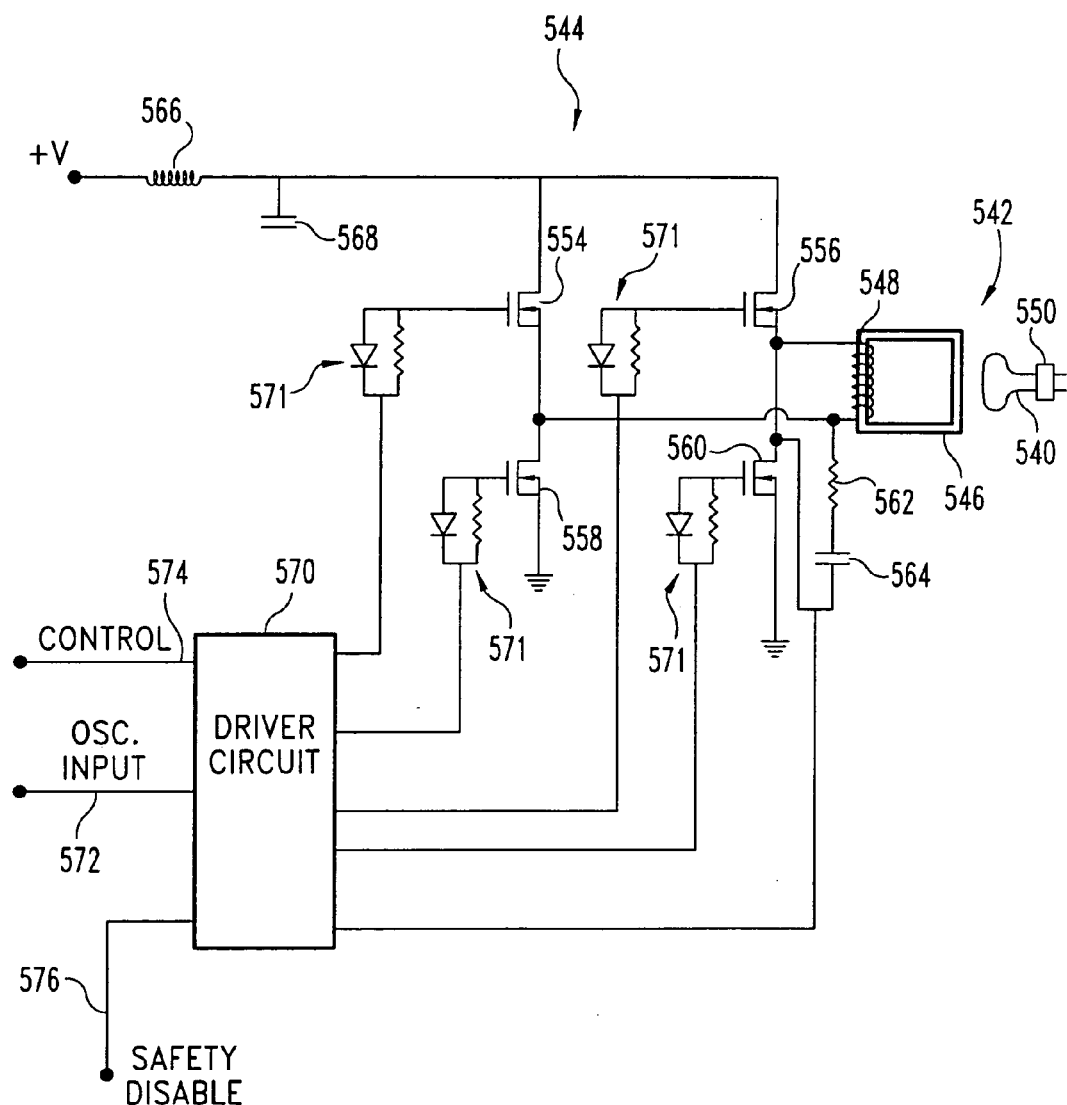
FIG. 26 is a schematic diagram of one embodiment of a driver circuit for the heater shown in FIG. 25.

During operation of heater 25, current flow in primary windings 548 induces current to flow in the transformer secondary winding, i.e., loop 540. The electrical resistance of the tubing of loop 540 causes it to generate heat which is transferred to the fluid flowing through loop 540. Other configurations of transformer 542, including but not limited to the shape and size of loop 540, are of course possible, and the configuration shown is only for illustrative purposes. Referring to FIG. 25, the details of the structure and operation of one embodiment of drive circuit 544 will now be described. Where reference is made to specific components or component values, such reference is for illustrative purposes only; other equally suitable configurations that fall within the spirit of the invention are contemplated as well.

Field Effect Transistors (FETs) 554, 556, 558, and 560 are avalanche rated at 200 V to accommodate the inductance of transformer 542 (including loop 550), and are connected in a conventional H-bridge design. FETs 554, 556, 558, and 560 are specifically designed to handle unclamped inductive loads. Resistor 562 and capacitor 564 snub high frequency ringing. Inductor 566 and capacitor 568 provide filtering for the power supply. Additionally, capacitor 568 provides energy storage to act with the load inductance. A relatively high capacitance value is needed to accommodate ripple current. FET gate driver circuit 570 is a fast, high current device with the ability to control shoot-through current, such as, for example, an integrated circuit identified as HIP4080A, manufactured by Intersil Corporation. Circuits 571, shown connected to the inputs of each FET, provide turn on/turn off delay and anti-oscillation for FETs 554, 556, 558, and 560. The signal on control input 574 utilizes the oscillator input signal on input line 572 to control the switching of FETs 554, 556, 558, and 560.

FETs 554 and 560 will conduct during one half of each oscillator cycle, while FETs 556 and 558 conduct during the other half cycle. Conduction of each pair of FETs causes current to flow in primary winding 548 of transformer 542, thereby inducing current to flow in the secondary of transformer 542, which comprises loop 550.

The power output of transformer 542, and hence the degree of heating of loop 550, may be controlled by varying the driver frequency via oscillator input 572. This is due to the inductance in the stainless steel tubing of loop 550. Acceptable power transfer and heating may be obtained with driver frequencies that range from about 24 kHz to approximately 40 kHz. Below about 24 kHz, oscillator noise becomes audible and power consumption becomes excessive due to magnetic saturation of core 546. Above about 40 kHz, transformer core losses, skin resistance, and low power factor of transformer 542 begin to become unacceptable. Control input 574 may also be used to force the switching of one or more of FETs 554, 556, 558, and 560, thereby acting to turn heater 25 on and off. Safety disable input 576 causes all of the FETs to switch to an off-state, such as if a transformer secondary overvoltage condition were detected, in order to prevent damage to heater 25 or injury to a patient.

Additional enhancements to heater 25 may also be added, including but not limited to, a microcontroller for controlling the operation of heater 25 by monitoring FET heat sink and loop 550 temperature. The microcontroller may also monitor power consumption and adjust the FET drive waveform and frequency appropriately. Heater reliability is improved by monitoring heat sink temperature, i.e., FET junction temperature, of FETs 554, 556, 558, and 560. If heat sink temperature becomes too high, heater 25 may be shut down or the driver frequency increased to decrease power output.

The impedance of the secondary winding of transformer 542 is partly a function of the resistance of loop 550, but it is primarily influenced by loop inductance. For that reason, transformer power can be controlled by the driver frequency. A microcontroller can be use to simply raise the driver frequency to reduce heater output.

Figure 8:
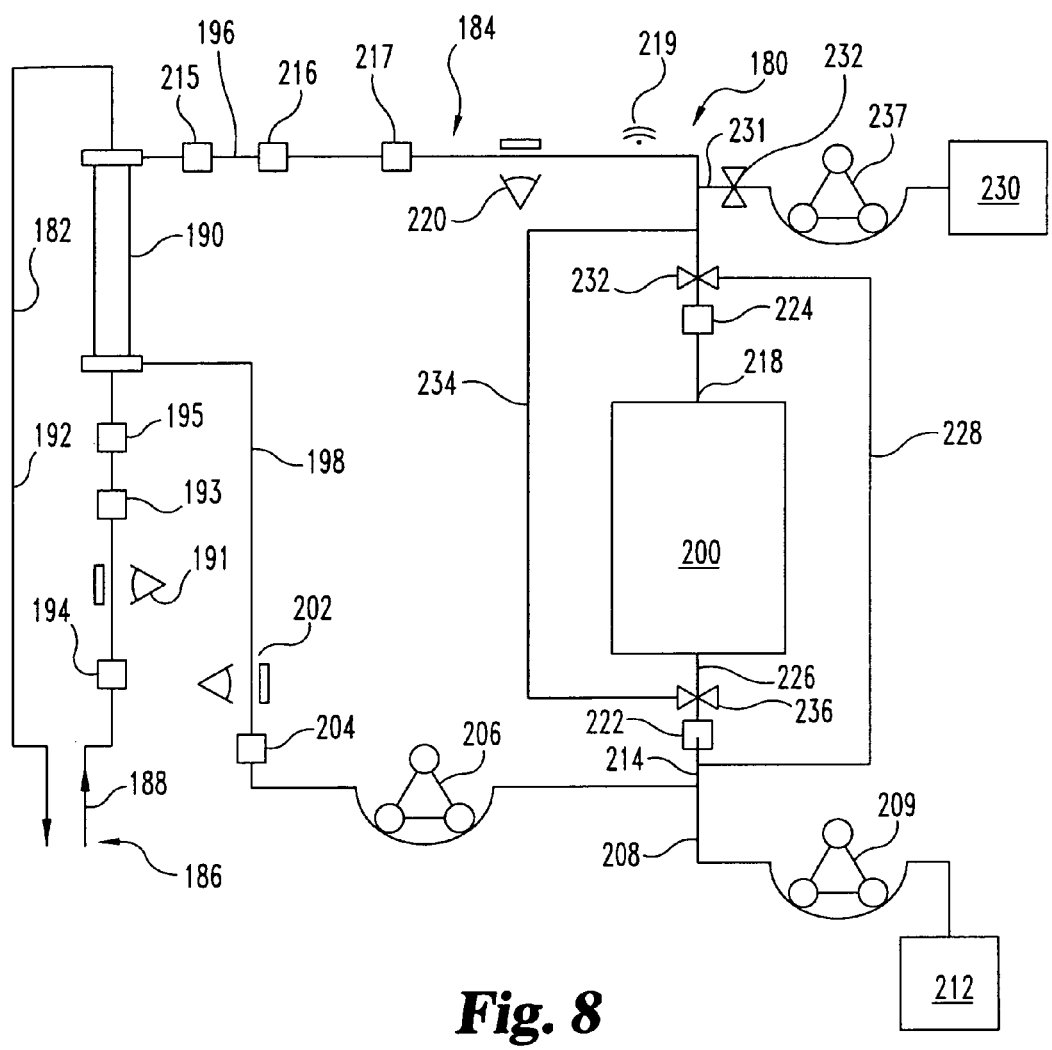
FIG. 8 is a schematic representation of an extracorporeal blood circuit incorporating a hollow fiber plasma filter and a sorbent reactor in series in accordance with the present invention.

FIG. 8 is a schematic representation of a treatment system 180 including a sorbent reactor in accordance with the present invention. System 180 includes a blood flow circuit 182 and a treatment fluid circuit 184. Starting from patient access 186, blood inflow line 188 leads to separation device 190. Blood circuit 182 can include one or more blood pumping devices 194, such as pumping device 21 in blood circuit 12 in system 10, using whatever pumping technology is appropriate. Line 192 extends from separation device 190 back to the patient access 186. Additionally, the blood circuit can include one or more safety monitors to measure blood flow and the pressure inside the inflow line 188 and/or line 192, for example, optical monitor 191, blood flow meter 193, and pressure transducer 195.

Treatment fluid circuit 184 includes line 196 from reactor 200 leading to separation device 190, and line 198 leads from separation device 190 to sorbent reactor 200. Line 198 can include one or more monitors such as optical monitor 202 and pressure transducer 204 to measure fluid pressure and the presence or absence of various components including red blood cells, solid sorbent particles, and the like. Various pressure transducers, optical monitors, and flow meters are known in the art and can be used in the present invention. Specific examples are listed in U.S. Pat. Nos. 5,277,820; 5,919,369; and 6,348,162, each of which is incorporated herein by reference in its entirety.

In certain preferred embodiments, the fluid volume in treatment fluid circuit 184 is maintained at a constant volume. This ensures that the patient neither gains nor loses fluid. Alternatively, if desired or deemed medically expedient, the volume of treatment fluid can be varied to ensure that the patient either gains or loses fluid or that the patient's fluid volume remains unchanged. One or more outflow lines 208 can be connected to circuit 184. When desired, an amount of the treatment fluid can be diverted from the treatment fluid circuit through line 208 using fluid removal pump 209. In the illustrated embodiment, outflow 208 allows removal of excess fluid. The removed fluid can be collected and stored in reservoir 212, which can be monitored, for example by weighing, to ensure proper control of the fluid volume in system 180. The amount of fluid removed should be monitored to ensure that fluid removal control is correct during the process. Alternatively, pump 209 can be omitted, or optionally replaced with a simple valve or other control device, possibly including an orifice designed to pass a controlled amount of fluid, and diversion of treatment fluid through line 208 can be effected, for example, by pressure generated by pump 206. Additionally, line 208 may be connected at other points in the system.

Treatment fluid pump 206 forces the treatment fluid through line 214 and eventually into sorbent reactor 200. In some embodiments, reactor 200, if of the embodiment of 50, will have sufficient pumping action that pump 206 may be omitted. In such event, it may be desirable in some embodiments to move line 208 to connect with line 196. If included, pump 206 may be any type of pump, not necessarily the peristaltic pump depicted. Sorbent reactor 200 can be provided as has been described for reactors 50 or 90 in accordance with the present invention. The sorbent reactor 200 includes a sorbent suspension that has been homogeneously mixed and maintained as a suspension with minimal settling. This provides an efficient transfer of toxins from the treatment fluid to the sorbent particles.

Outlet 218 from reactor 200 leads to line 196 and eventually back to separation device 190. Additionally, outlet 218 and/or 196 can include a wide variety of optical monitors 220, ultrasonic bubble detectors 219, heaters 215, filters 216, and gas removers 217 as indicated.

Preferably one or more pressure transducers 222 and 224 are positioned near the inlet 226 and/or outlet 218 of reactor 200. Pressure transducers 222 and 224 allow the pressure drop across reactor 200 to be monitored. If the pressure drop becomes too great, remedial procedures can be invoked to continue blood treatment so that the patient remains safe and comfortable. Such remedial procedures can include, for example, diverting treatment fluid flow from reactor 200 through one or more bypass lines 228.

In one preferred embodiment of the present invention, reactor 200 is provided that has the general configuration as described for reactor 50. In this embodiment, line 234 and valve 236 would not be included in the system. If during treatment the pressure drop across reactor 200 is too great, then the treatment fluid can be diverted (in whole or part) through bypass line 228 using valve 232, which valve also blocks flow out of reactor 200. Consequently some or all of the treatment fluid does not exit reactor 200. However, a rotor such as rotor 74 inside reactor 50 can continue to rotate to remove any deposition of the solid components of the sorbent suspension from the filter positioned inside the reactor. Since the flow across filter 64 is zero or reduced, the differential pressure also becomes zero or reduced, and accumulations of sorbent may be removed by the action of rotor 74. Should it be not desired to completely stop outflow from reactor 200, valve 232 may be implemented as a simple one-way valve in line 228 or can have alternative configurations to achieve partial bypass of treatment fluid.

Additionally, if reactor 50 is employed at reactor 200, when it may be desired to clear the filter 64 of an accumulation of sorbent, the rotor of reactor 200 may continue to turn while the output line 218 is closed by valve 232 or any other means such as a tubing clamp. In this embodiment, valve 236 and bypass lines 234 and 228 are not included. Because there is no fluid bypass, pump 206, if included, must also be stopped as well. Since the flow across filter 64 is zero, the differential pressure also becomes zero and accumulations of sorbent may be removed by the action of the rotor. Similarly to above, fluid flow may be merely reduced, stopped.

In other embodiments, reactor 200 can be provided that has the general configuration as described for reactor 90. If it is determined in use that the pressure drop across reactor 200 is too great, treatment fluid can be diverted first through bypass line 228 and then introduced into reactor 200 through outlet 218 by means of three-way valve 232. The treatment fluid will thus flow through reactor 200 in a direction opposite that it flowed before being diverted. Treatment fluid can then exit reactor through inlet 226. From inlet 226 the filtrate will flow through three-way valve 236 into the second bypass line 234 and thence to line 196. Reversing the treatment fluid flow through the reactor 200 can allow the treatment fluid to remove and re-suspend any solid component of the sorbent suspension that deposited on one or the other membrane/filters inside reactor 200 as above described for reactor 90.

Additionally, if desired or deemed medically prudent, various beneficial components can be introduced into the treatment fluid. The additives can be provided in reservoir 230 and introduced through line 231, preferably using a fluid pump 237. The additives can include a wide variety of components to facilitate compatibility of the treatment fluid with the blood. In other embodiments, line 231 may connect to circuit 184 at another point in line 196 or 198 rather than the point shown.

In an alternate embodiment of the invention, a safety filter may be incorporated in line 196 in order to preclude the contents of the reactor from entering the patient's blood stream in the event of a reactor filter failure. Such a safety filter is not necessary when the pore size of the filter is sufficiently small to perform this function or if the monitors for sorbent particles in the return line are sensitive enough and respond fast enough to prevent passage of significant amount of sorbent in case of a filter rupture.

Anticoagulation is a major concern in all extracorporeal treatments. One of the major advantages of the DT System over one of its predecessors, hemoperfusion, is the reduced disruption of the coagulation system of the patient. The DT System uses a dialyzer membrane to separate the formed blood components from the charcoal sorbent. This dramatically reduces the coagulation problems encountered with many hemoperfusion columns. The present invention enhances this advantage of the DT System in two ways. First, the invention makes possible the use of more modern dialyzer or plasmafilter membranes. Second, the invention enables the use of regional anticoagulation to maximize the longevity of the treatment while minimizing the effect on the patient.

Figure 9:
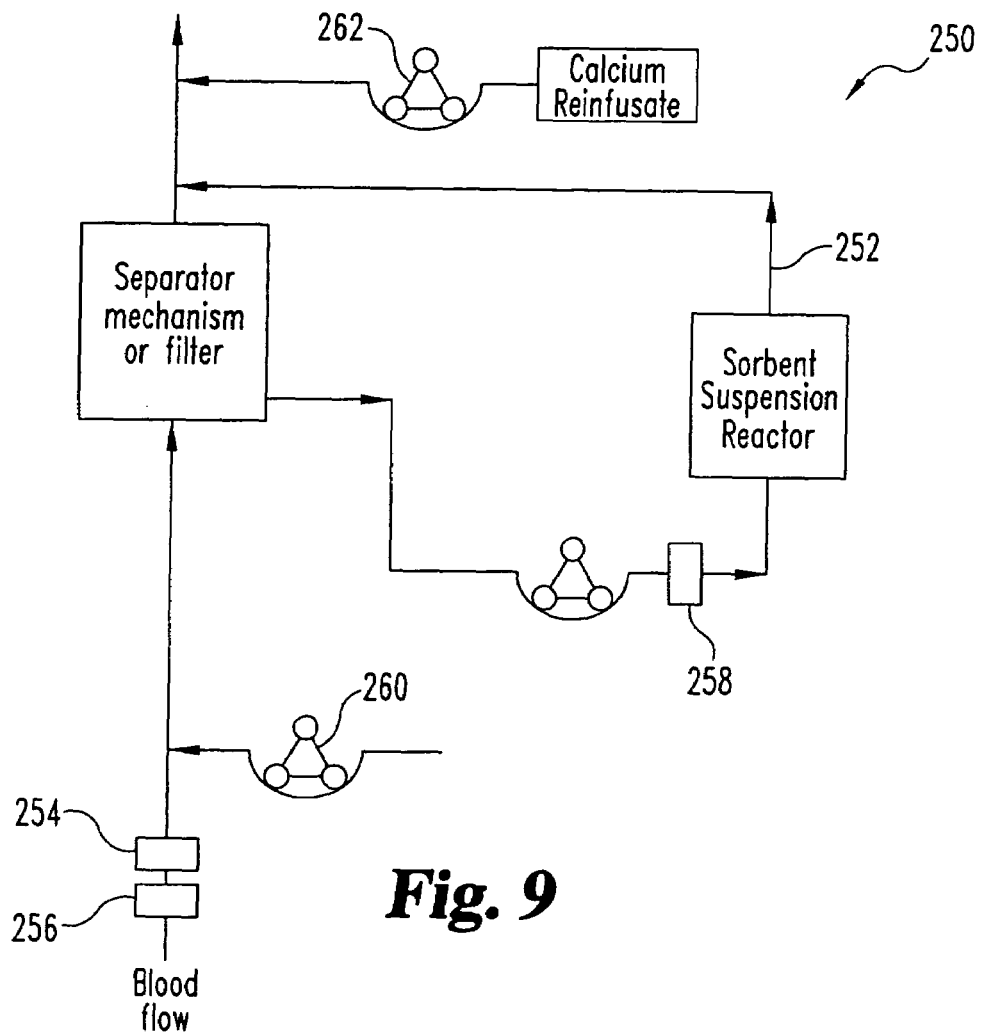
FIG. 9 is a schematic representation of a regional anticoagulation system for a sorbent reactor.

One embodiment of a regional anticoagulation system 250 is shown in FIG. 9. System 250 anticoagulates the extracorporeal circuit 252, and it should have minimal effect on the coagulation status of the patient because the anticoagulant effect is localized to the extracorporeal circuit. The system 250 measures the concentration of calcium and the blood flow rate with meters 254 and 256, respectively. From that information, the amount of citrate required to anticoagulate is known. The citrate anticoagulant can be added to the patient's blood using a controllable pump 260. In the preferred embodiment, downstream of the citrate infusion, the calcium concentration is measured at sensor 258. This will check the accuracy of the citrate infusion.

Calcium is added to the blood returning to the patient via a controllable pump 262. Preferably, calcium is combined with the treated blood, as close to the patient is possible. Calcium sensor 254 on the blood inflow line controls the operation of the calcium reinfusate system, not only with a view to determining citrate infusion as described above, but also to detect trends in the patient calcium level which may be indicative of calcium reinfusate malfunction or the patient's inability to metabolize citrate. The goal is to keep the extracorporeal circuit properly anti-coagulated without anticoagulating the patient. The desired ionized calcium concentration in the extracorporeal circuit is about 0.25 mM; desired ionized calcium concentration in blood is about 1.0 mM. Removing calcium from the blood is a very effective anticoagulation method because calcium is essential to all clotting pathways. Citrate is one of the most effective and safe calcium chelating agents available.

In a preferred embodiment, the system can include two feedback loops between sensors 254 and 258 and pumps 262 and 260, respectively. For example, the calcium sensor 258 on the extracorporeal circuit can detect ionized calcium and a feedback loop to the citrate pump 260 can vary the rate (or amount) of citrate infusion to keep ionized calcium at a desired level, preferably for humans at 0.25 mM. A calcium sensor 254 on the blood inflow line can also be used to detect the ionized calcium and a feedback loop can control pump 262 to vary the calcium infusion rate to maintain this at normal levels of about 1 mM. In this embodiment, the system works in spite of varying body metabolism of citrate, and it also detects a malfunction of any of the citrate or calcium infusion pumps.

Figure 10:
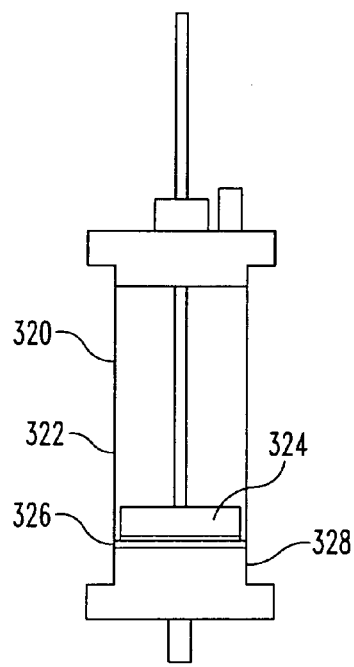
FIG. 10 is an illustration of a flat-plate reactor in accordance with the present invention.
Figure 11:
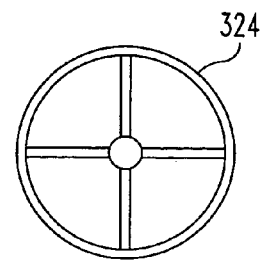
FIG. 11 is a partial end view of one embodiment of a stir bar for the flat plate reactor.
Figure 12A:
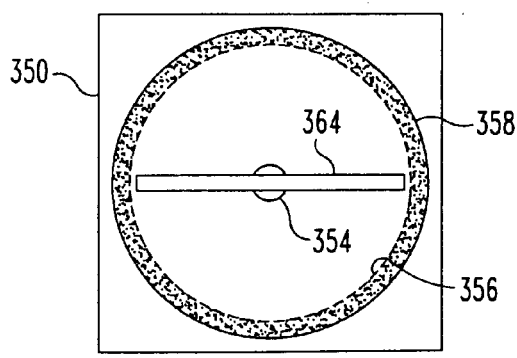
FIG. 12A is a cross-sectional view taken along section line 12A—12A of the reactor of FIG. 12.
Figure 12:
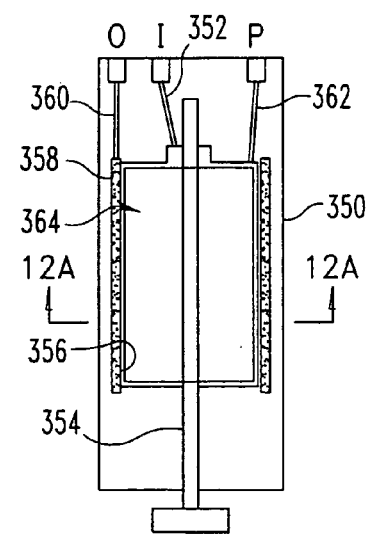
FIG. 12 is an illustration of a centrifugal reactor in accordance with the present invention.

The principles of the invention can be achieved using a wide variety of reactor configurations, and prototypes of two preferred arrangements that were constructed and used in experimental testing are set forth schematically in FIGS. 10 and 12. FIG. 10 depicts a Flat Plate reactor 320, consisting of a 250 mL vessel 322, which contains the sorbent suspension. FIG. 11 is an end view of a cross shaped stir bar 324, which can rest just above the filter 326, a Pall Corporation "Supor" 0.2 µm high flow membrane filter. The rim of the stir bar 324 prevents accidental contact with the membrane filter. The filter holder 328 supports the membrane filter 326 and provides a membrane filter support through which fluid may flow through to the outlet.

FIGS. 12 and 12A depict a centrifugal reactor 350 which, although it is in a different geometrical configuration, operates on the same general principles as reactors 300, 320, and which may, optionally, pump the fluid as well in a manner similar to a standard centrifugal pump. Treatment fluid enters port 352 near the shaft 354, flows through the reactor 350, where it is mixed with the sorbent suspension, then moves across the membrane filter 356, through the membrane filter support system 358, and thence to the outlet 360. Transmembrane pressure may also be monitored at test port 362. In the illustrated embodiment, impeller 364 is a simple flat plate whose edges are approximately 2.5 mm from the filter. The filter is also held in place by a wire screen (not shown).

Each of the two reactor configurations 320 and 350 has been tested in multiple trials. In certain selected trials, discussed more fully below, most operating conditions were similar enough to permit comparisons between the two types of reactor (Flat Plate and Centrifugal) and also to a full sized production reactor. Table 1 compares the reactors and their respective operating conditions to a contemplated production version of each type. Table 1 gives conditions for both the flat plate reactor 320 and the centrifugal reactor 350. The flat plate reactor 320 tests employed an external peristaltic pump and an external rotor drive set to 1500 RPM, while the centrifugal reactor 350 tests used a PID algorithm to adjust the rotor speed to provide a constant flow using the reactor itself as a centrifugal pump. For convenience, deionized water was used as the treatment fluid. The reactors 320 and 350 were allowed to run without operator intervention for a minimum of 4 hours.

TABLE 1

Reactor Parameter Comparison Table
(Some numbers are estimates for production versions)

|  | Flat Plate | Centrifugal | Production Flat Plate | Production Centrifugal |
| --- | --- | --- | --- | --- |
| Internal Diameter (cm) | 5 | 8 | 27 | 15 |
| Internal Length (cm) | 12 | 6 | 3.6 | 12 |
| Useful Volume (Vv, mL) | 250 | 290 | 2000 | 2000 |
| Membrane Area (Am, cm$^2$) | 13.1 | 147 | 547 | 547 |
| Initial Rotor Speed (RPM) | 1500 | 1000 | 500 | 800 |
| Mean Rotor to Membrane Velocity (cm/s) | 80 | 419 | 419 | 628 |
| Flow Rate (Q, mL/min.) | 11 | 129 | 450 | 450 |
| Charcoal Load (g) | 17.5 | 20.3 | 140 | 140 |
| Flow per Unit Area ((mL/min.)/cm$^2$) | 0.84 | 0.82 | 0.82 | 0.82 |

Figure 13:
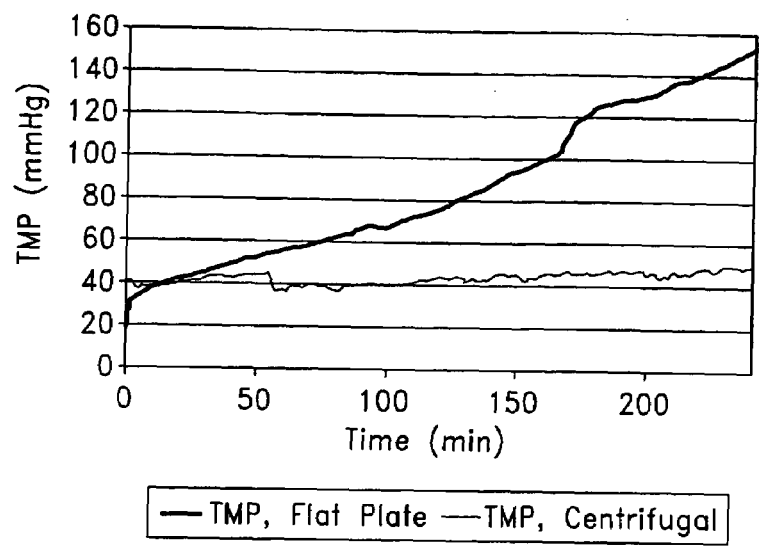
FIG. 13 is a graph plotting the transmembrane pressure (TMP in mmHg) over 4 hours for the flat-plate reactor and centrifugal reactor of FIGS. 11 and 12, respectively.
Figure 14:
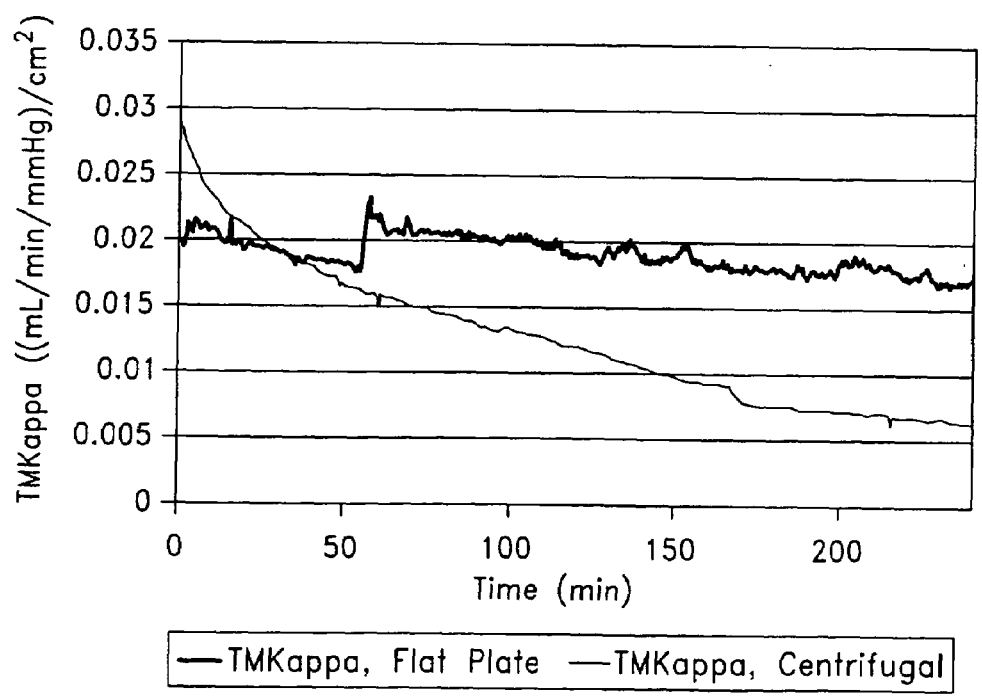
FIG. 14 is a graph plotting the transmembrane pressure normalized for the transmembrane flow (TMF) and the membrane effective surface area for the flat-plate reactor and the centrifugal reactor of FIGS. 11 and 12, respectively.

The results of these trials are shown in FIGS. 13 and 14 and in Table 2. The term "TMP" refers to Trans Membrane Pressure, i.e. the pressure difference across a membrane in mmHg. This includes pressure due to any charcoal cake formation, and resistance caused by the filter backing and flow passages between the filter and outlet port of the reactor. The term "TMκ" refers to Trans Membrane Permeability per square cm. TMκ is determined by first determining Trans Membrane Resistance ("TMR"), which is defined as the effective resistance of the membrane to flow (mmHg/(mL/min)). Next, Trans Membrane Permeability ("TMµ"), which is the inverse of TMR ((mL/min)/mmHg) is determined. TMκ ((mL/min)/mmHg)/cm$^2$) is then calculated by dividing TMµ by area (TMµ/Area), which provides a basis of comparing results from different membrane areas. It is worthy of note that, since there are some second order effects, the best comparisons are made on the basis of equal flow per unit area (mL/min/cm$^2$) of membrane.

TABLE 2

Reactor Results Table

|  | Flat Plate | Centrifugal |
| --- | --- | --- |
| Short Term TMP | 27 | 31 |
| Beginning TMP at Start of 4 Hour Run | 40 | 19 |
| Ending TMP after 4 Hour Run | 64 | 153 |
| Ending TMP after Clearing Operation | 64 | 78 |
| Short term TMκ | 0.030 | 0.028 |
| Beginning TMκ at Start of 4 Hour Run | 0.020 | 0.029 |
| Ending TMκ after 4 Hour Run | 0.017 | 0.006 |
| Ending TMκ after Clearing Operation | 0.017 | 0.018 |

Based upon the results of these tests, both reactors are shown to provide good functionality, and the results are fairly comparable if the membrane is cleared of charcoal.

The cylindrical reactor had an increasing TMP during the 4-hour experiment while the TMP for the flat-plate reactor was nearly constant.

Not shown in FIG. 13 or 14 are the results of a charcoal clearing operation for the centrifugal reactor to remove accumulated charcoal (a flow perturbation step). This was done only after the 4 hours were complete to avoid perturbing the experiment. TMκ was increased to 0.18 by this operation.

Provided that adequate charcoal clearance is maintained, either reactor configuration will provide satisfactory results in terms of the goals of: (1) thorough exposure of treated fluid to large surface area of charcoal, (2) continuous operation, (3) charcoal and other sorbents segregated from remainder of system, and (4) simple leak detection. For the experiments described above, the two versions of a Sorbent Suspension Reactor (SSR) allow unidirectional flow of solution through a thick suspension of powdered charcoal sorbent suspension with retention of all sorbent particles by a single membrane. The devices have been tested in conditions simulating treatment of dialysis fluid for removal of toxins. Results indicate that flow rates of dialysate through reactors with modest size membrane area (547 $cm^2$) and modest pressure drops can be maintained for 4 hours or more at 450 ml/min. This means that a standard hemodialysis machine could be used for treatment of patients with hepatic failure, with an add-on module used to regenerate a small amount of dialysate by directing it through the SSR and returning dialysate to the dialyzer. The sorbent suspension would selectively remove toxins from the dialysate and return some nutrients (if the sorbents were pre-equilibrated with these nutrients). The add-on device including the SSR would be quite simple, having as its main components only a reactor with rotor drive, a secondary safety filter (optionally), an optical monitor to detect membrane leakage, a pressure monitor, and a roller pump (the roller pump could be omitted in the centrifugal design). A communication interface to the add-on module to the dialysis machine is not necessary. The result is that any dialysis or hemofiltration machine can be adapted to treat patients with liver failure, using the powerful adsorptive capacity of powdered sorbent suspension for selective toxin removal. Newer sorbents such as zirconium silicate added to the SSR could greatly increase removal of ammonium and other cationic toxins.

To transfer protein bound toxins from blood to dialysate and then remove the toxins with sorbents, it has been proposed to add albumin to the dialysate and use a high permeability dialyzer of polysulfone or other material. A commercially available product referred to as the MARS device (Molecular Adsorbent Recirculating System) has demonstrated that the albumin does promote the transfer of bilirubin, bile acids, and other protein-bound toxins across the high permeability dialyzers. However, studies have also demonstrated that the small columns of charcoal and anion exchangers in the MARS device become saturated with toxins long before the end of the treatment. With the SSR, albumin could be added to the dialysis circuit. The resulting albumin/dialysate solution would be treated by the powdered sorbents with a very high capacity for protein-bound toxins. It is expected that the flow rate of dialysate would be about 250 ml/min, which is high enough to result in much higher clearance of protein-bound and water soluble toxins than the MARS system, with less cost and complexity.

To remove protein-bound toxins even more effectively, the SSR can be used to detoxify plasma leaving a membrane or centrifugal plasmapheresis device. In addition, it could be used to convert any hemodialysis machine into a plasmapheresis device by using a plasmafilter and the pressure monitors in the treatment fluid circuit of the sorbent reactor. Flow rate in this case would be whatever plasma flow rate can be generated by the pheresis device or filter, usually up to 60 ml/min. This application can remove toxins bound to albumin as well as toxins bound to globulins, such as cytokines. Also in this application immunotherapy would be improved, providing very large surfaces of powdered charcoal or silica for binding antigens or antibodies to continue for many hours without saturation of the sorbent (as is seen in column therapies with Staph Protein A and various immunoglobulins).

Figure 15:
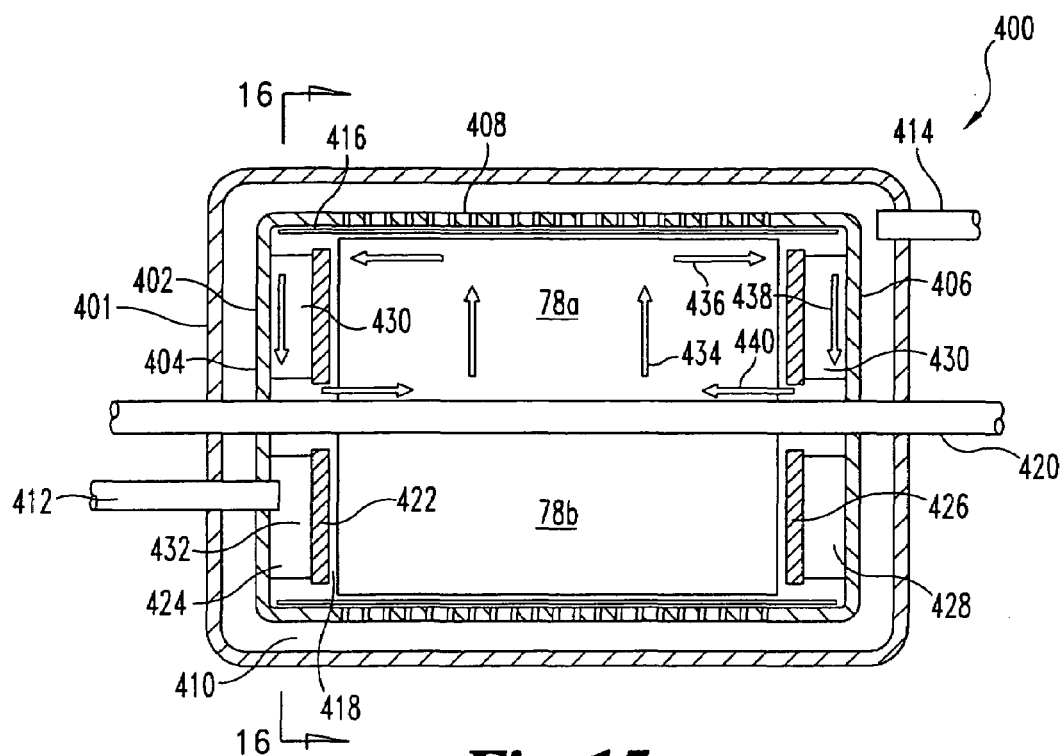
FIG. 15 is a cross-sectional view of an alternative embodiment of a sorbent reactor for use in the extracorporeal treatment of blood in accordance with the present invention.

FIG. 15 illustrates still yet another embodiment of the invention, including a reactor 400, which can be employed in the extracorporeal treatment of blood in accordance with the present invention. Reactor 400 is illustrated as a centrifugal reactor having an external housing 401 and an internal housing 402. Housing 402 includes a first end wall portion 404, a second end wall portion 406, and a porous, cylindrical side wall portion 408 therebetween. External housing 401 defines an interior chamber 410. A filtration membrane 416 is disposed in the interior chamber and partitions the interior chamber 410 to provide an inner region 418. Additionally, reactor 400 can include an inlet 412 into inner region 418 and an outlet 414 from interior chamber 410. A rotatable rotor 420 extends through reactor 400. Rotor 420 can be provided as has been substantially described for rotor 74 including a shaft 76 and one or more oppositely extending paddles 78a and 78b.

Figure 16:
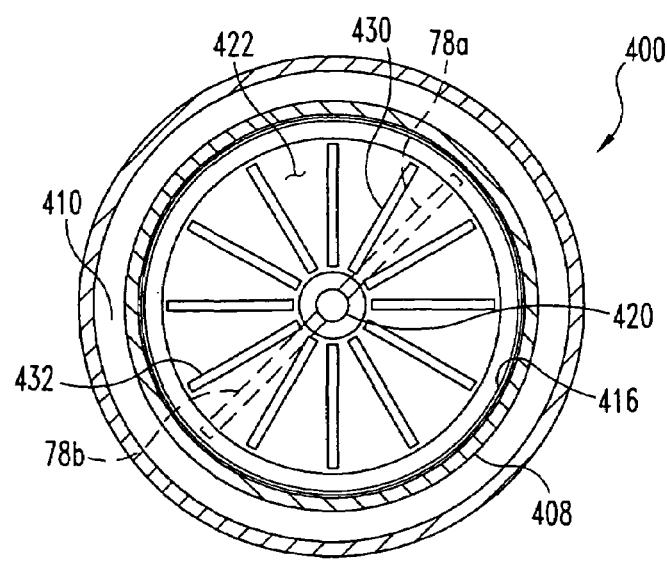
FIG. 16 is a cross-sectional end view of the sorbent reactor of FIG. 15.

Referring additionally to FIG. 16, reactor 400 can include one or more interior partitions 422, 426. In the illustrated embodiment, reactor 400 includes a first partition 422 positioned adjacent first end wall portion 404. Consequently, first partition 422 defines a shunt chamber 424 between first partition 422 and first end wall portion 404. Additionally, a second partition 426 is positioned adjacent second end wall portion 406 and defines a second shunt chamber 428 between second partition 426 and second end wall portion 406.

In operation, a rotation of rotor 420 and paddles 78a and 78b creates a centrifugal force, forcing the sorbent suspension against the side wall portion 408 and the filter membrane 416 secured thereto which allows the treatment fluid to pass through. This can result in the polarization or accumulation of the solid sorbent particles on the filter membrane, which in turn can reduce the flow and/or block the flow of the treatment fluid out of the reaction chamber. In the illustrated embodiment, however, the rotation of the rotor causes a relatively high pressure at the location of filter member 416, which urges or forces the sorbent suspension to flow in a direction parallel to the axis of the rotor towards the first and second end wall portions 404, 406. Consequently, the sorbent suspension can flow through the shunt chambers 424 and 428 toward the shaft 76 of rotor 420. This flow is illustrated generally in FIG. 15 as reference lines 434, 436, 438, and 440. This allows greater mixing of the treatment fluid and the solid adsorbent particles within reactor 400, and additionally provides a mechanism to reduce the polarization or accumulation of the solid adsorbent particles along the surface of filtration membrane 416.

The reason for this reduction in polarization and sorbent accumulation is as follows. In the reactor of FIGS. 2, 3, the rotating fluid mass behaves much like a centrifuge, creating a substantially higher pressure near the filter 416 than at the axis. Sorbent concentration thus would tend to increase near the circumference relative to the axis. However, provided that the fluid within the shunts 424, 428 is non-rotating, and provided that fluid flow resistance within the shunts 424, 428 is minimal, the pressure difference between the axis and circumference is greatly reduced or minimized. The reactor thus ceases to behave like a centrifuge and sorbent distribution is much more uniform between the axis and circumference. Uniformity of sorbent concentration is also enhanced by the mixing action provided by the flow depicted by arrows 434–441.

In the embodiment depicted in FIGS. 15 and 16, a plurality of vanes or fins 430 and 432 extend from first and second partitions 422 and 426, respectively. Fins 430 and 432 direct the sorbent suspension to flow through the shunts in a radial direction toward the shaft 76 of rotor 420, thus preventing centrifugal movement of the sorbent suspension in shunt chambers 424, 428.

It will be observed that fluid must enter at the circumference of shunt plate 422, 426 (arrow 436). Hence, since the fins/vanes extend from the shunt plate 422, 426 to the wall of the reactor 404, one embodiment of the shunted reactor system is to use the fins to join the plates 422, 426 to the wall 404. Another embodiment would be to use any type of standard fastening system such as screws to press shunt plates 422, 426 against wall 404, thus securing the shunt plates to the rest of the reactor. Other attachment methods such as adhesive bonding or thermal welding, struts extending from the circumference of the reactor to the shunt plates 422, 426, and the like which are known to those skilled in the art are also contemplated by the invention.

Figure 17:
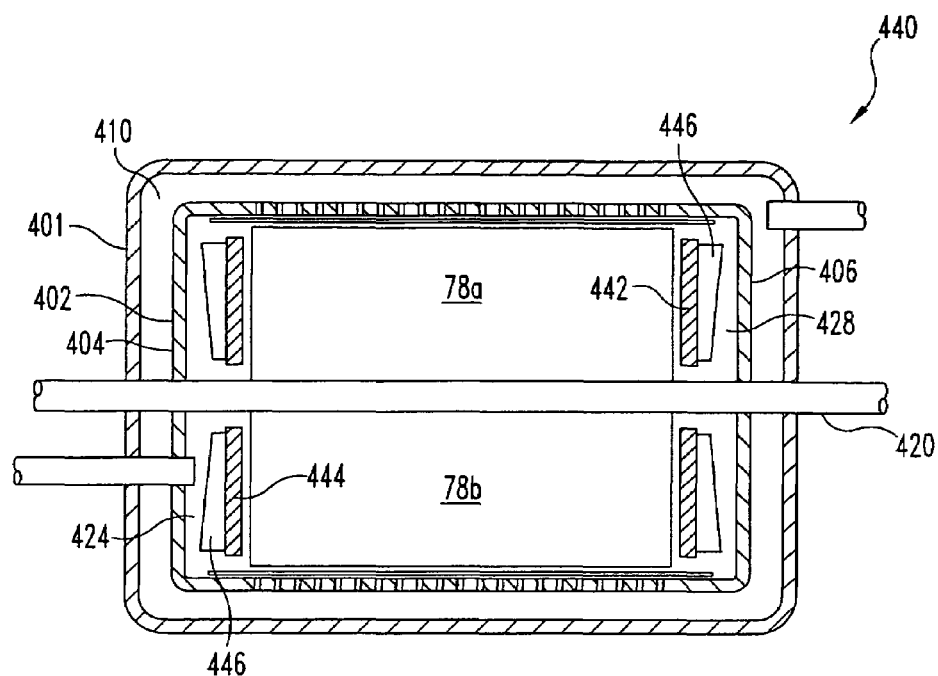
FIG. 17 is a cross-sectional view of still yet another embodiment of a sorbent reactor for use in the extracorporeal treatment of blood in accordance with the present invention.

FIG. 17 is still yet another embodiment of a centrifugal sorbent reactor 440 in accordance with the present invention. Reactor 440 is formed similarly to reactor 400 and, consequently, the same reference numbers will be used to denote like components. Reactor 440 includes an outer housing 401 defining an interior chamber 410 and an inner housing 402 and a rotor 420 having at least a pair of opposing paddles 78a and 78b extending therethrough. Additionally, reactor 440 includes a first and second partition 442 and 444, respectively. Each of partitions 442 and 444 in conjunction with the respective first and second end wall portions 404 and 406 define shunt chambers 424 and 428. Additionally, partitions 442 and 444 include a plurality of fins 446. Fins 446 can be provided in a variety of configurations, each configuration provided as a narrow vane extending radially from the location of rotor 420. In a preferred embodiment, fins 446 are provided as tapering defining an angled inlet adjacent the rotor 420. This provides additional advantages in reducing the tangential velocity of the fluid/suspension induced by the rotor. Fins 446 are provided to inhibit or eliminate centrifugal movement or rotation of the sorbent suspension in the shunt chambers 424, 428. In a preferred embodiment, the shunt chamber has a uniform cross-sectional area to maintain a constant fluid velocity therethrough. Consequently, the plurality of fins 446 serve to both smoothly direct fluid flow and induce a non-rotating flow through the shunt chamber.

Figure 18:
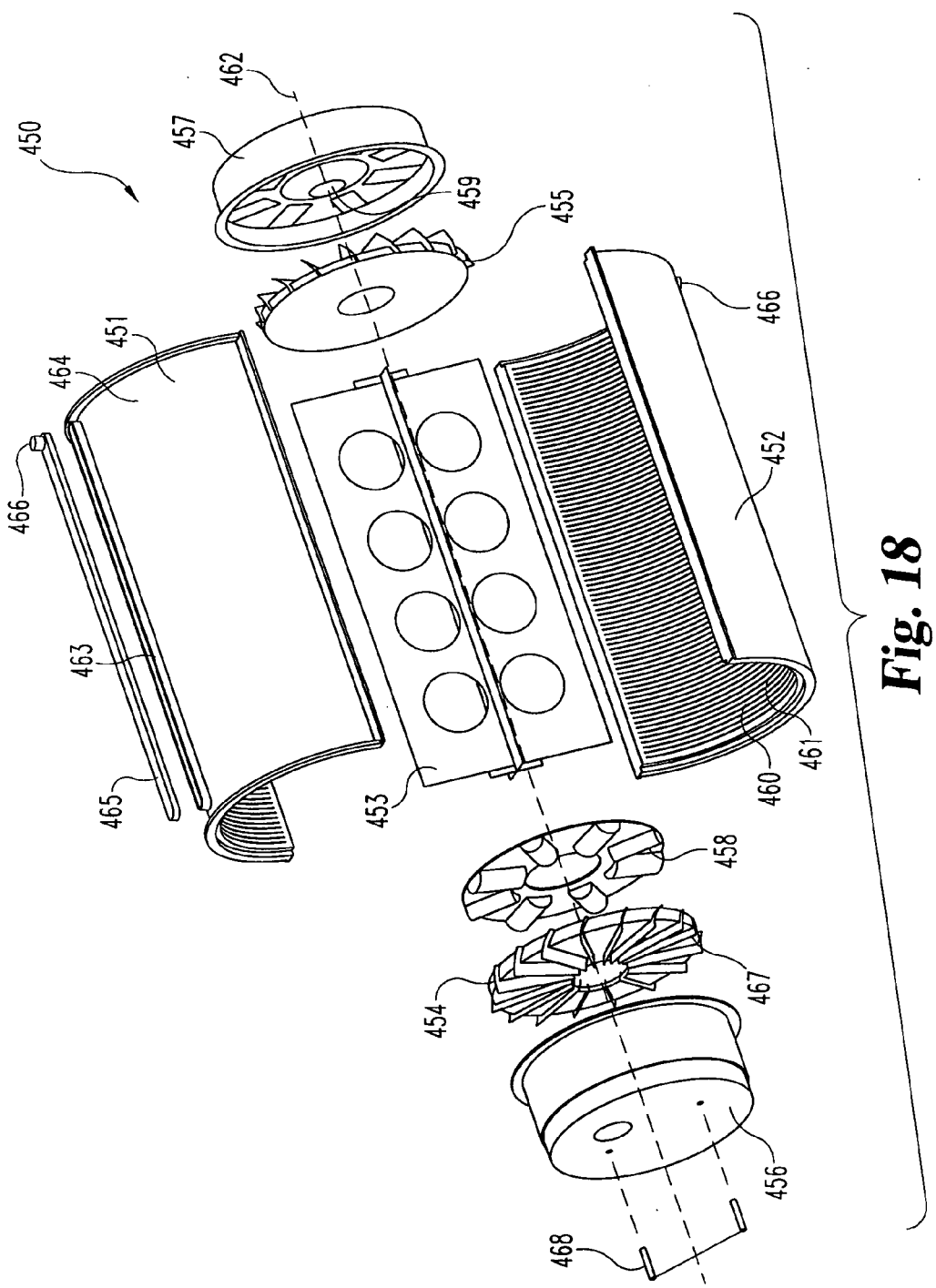
FIG. 18 is an exploded view of yet another embodiment of a sorbant reactor for use in accordance with the present invention.

FIG. 18 is an exploded view of yet another embodiment of a centrifugal sorbent reactor 450 in accordance with the present invention. Reactor 450 includes a housing formed of a first and second cylindrical shell portions 451 and 452 and first and second end wall portions 456 and 457 to define an interior chamber therebetween. In a preferred embodiment, shell portions 451 and 452 are mirror images of each other; consequently, the same reference numbers will be used for like structures. Second end wall portion 457 defines an inlet 459 providing a passage for a fluid/suspension into the interior chamber. A rotatable rotor 453 is positioned in the interior chamber. A first shunt plate 454 is positioned in the interior chamber adjacent first end wall portion 456. Similarly, a second shunt plate 455 is positioned in the interior chamber adjacent second end wall portion 457. Each of shunt plates 45 and 456 include a plurality of fins or vanes 467 to direct the flow of an included sorbant suspension through shunt chambers defined between first shunt plate 454 and first end wall 456; and between second shunt plate 455 and second end wall 457, respectively. In the illustrated embodiment it can be observed that the vanes 467 are angled radially and axially, as defined by longitudinal axis 462, to urge the sorbent suspension to circulate within the interior chamber. In one embodiment, shunt plates 454 and 455 can be secured to the respective end walls 456 and 457 with one or more pins 468. Consequently, shunt plates do not rotate within the interior chamber Magnetic drive plate 458 is positioned in the interior chamber adjacent shunt plate 454. Drive plate 458 is affixed to rotor 453. Upon application of a rotating magnetic or electrical field, magnetic drive plate 458 rotates within the interior chamber and causes rotation of rotor 453. However, it will be understood that magnetic drive plate need not be included and alternative drive mechanisms as discussed above can be used to operate rotor 453.

First and second cylindrical shells 451 and 452 include a plurality of grooves 460 on an their interior surface 461. In the illustrated embodiment, each of the plurality of grooves 460 includes one or more openings (not shown) aligned along the interior surface 461 and extending in a line substantially parallel to longitudinal axis 462. The plurality of holes provide a passageway of the treatment fluid out of the grooves 460 into a channel 463 that extends along the exterior surface 464 of each of cylindrical shells 451 and 452. A collection cap 465 extends over each of the channels 463. An outlet port 466 is provided in collection cap 465 to allow passage of the treatment fluid back to the treatment circuit. A filter can be disposed in the interior chamber on or against inner surface 461 of each of cylindrical shells 451 and 452 to filter the treatment fluid and retain the sorbent suspension within the interior chamber.

Figure 19:
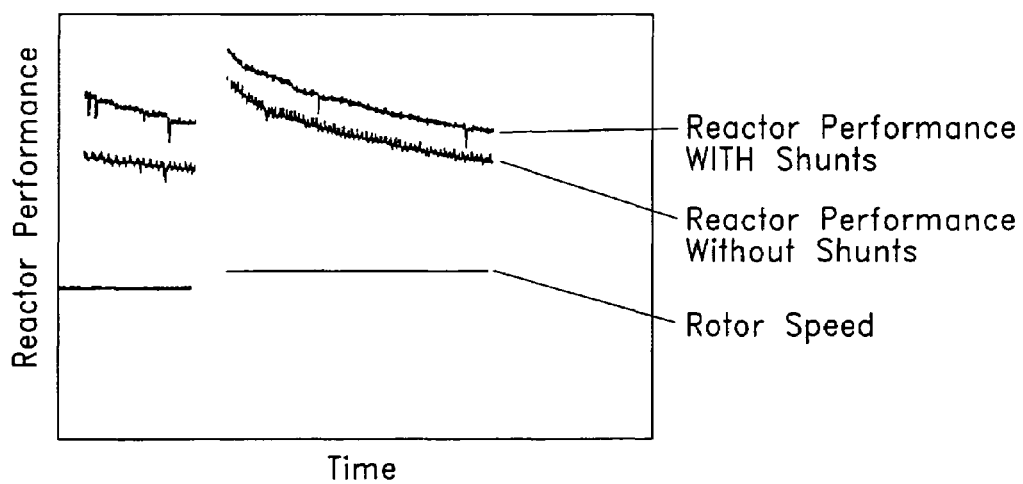
FIG. 19 is a graph comparing the performance of a centrifugal sorbent reactor including shunt chambers to the performance of a similar centrifugal reactor without shunt chambers.

FIG. 19 is a graph comparing the performance of a centrifugal reactor similar to that described above in FIGS. 2 and 3, to a centrifugal reactor with relatively small shunts as illustrated in FIG. 15. It can be observed from FIG. 19 that a substantial improvement results from the addition of the shunt chambers. The lowest trace near the Y-axis shows two different rotor speeds that were examined. At each rotor speed, the reactor efficiency declines over time due to accumulation of particles on the membrane. As can be seen from the graph, the performance gain due to the addition of shunt chambers within the reactor was substantial. In addition to substantially reducing the centrifugal effect, the shunt chambers significantly enhanced sorbent mixing by the addition of an axial flow through the circular flow pattern induced by the rotor.

In still other embodiments of the invention, multiple reactors can be used in a treatment system, each reactor being connected in series or in parallel with the others. An embodiment including multiple reactors in series may be useful, for example, in a treatment protocol in which treatment is more effective by successively treating the fluid in stages. An embodiment including multiple reactors in parallel may be useful, for example, where a high overall treatment fluid flow rate through the treatment fluid circuit is desired, while maintaining relatively low pressure gradients across any given sorbent filter. Multiple reactors in series or in parallel may also be useful for other reasons, such as, for example, in treatment protocols in which sorbent components desired for use are incompatible with one another. In addition or as an alternative to providing multiple reactors, the invention contemplates reactor designs defining discreet treatment fluid flow paths through multiple sorbent-containing elements within a single reactor housing. This, in effect, duplicates the results that can be obtained using multiple reactors in series.

In another advantageous aspect of the invention, a sorbent suspension reactor made or selected in accordance with the invention is used to provide a two-stage adsorbent system. A two-stage adsorbent system provided by the invention is an adsorbent system that provides functionality of a well-mixed sorbent suspension and also functionality of a stationary adsorbent device such as, for example, as adsorbent column. In one manner of achieving this dual functionality, an inventive sorbent suspension reactor is coupled in series to an adsorbent column. Alternatively, this dual functionality can be achieved in a single centrifugal sorbent reactor by control of operating conditions of the reactor.

To comment briefly on this dual functionality, it is well known to persons of ordinary skill in the art that a sorbent suspension reactor that maintains a well-mixed sorbent suspension is only one of many methods of bringing fluids in contact with particles in order to initiate reactions between the two. Another method is to pump fluid through a stationary layer of adsorbent. In a system for passing a fluid through a stationary layer of adsorbent, a filter retains the adsorbent in a container while allowing passage of fluid therethrough. Adsorption operations of this type are commonly implemented with stationary adsorbent in a column.

In a well-mixed system, such as a sorbent suspension reactor as described above, the amount of target substance adsorbed onto adsorbent particles, and the rate of adsorption, are functions of the amount of adsorbent available and the concentration of the target substance in the fluid. A column, however, behaves differently. Fluid enters a first port, or inlet port, typically at the top of a column, and exits at a second port, typically at the bottom of the column. The column is filled with stationary adsorbent. At the inlet port, the concentration of the target substance is high and so is the sorbent capacity. Anything not adsorbed near the inlet of the column will be adsorbed further down the column as the fluid passes through the column. The final effluent concentration is therefore close to zero. As fluid flow continues over time, however, the capacity of the adsorbent near the inlet becomes exhausted because the adsorbent in that area becomes saturated. As a result, the concentration of the target substance will not be reduced as the fluid passes through this region. The point of saturation will, over time, move toward the outlet port until the entire column is saturated. When the saturation point reaches the outlet of the column, the effluent concentration increases rapidly until it reaches the feed concentration.

Therefore, over time, the functionality of a well-mixed suspension system and a column adsorbent system are radically different. In a well-mixed system with a constant influent concentration, the effluent concentration steadily and smoothly increases over time as the sorbent capacity decreases. For applications where it is desired to minimize effluent concentration, this is a distinct disadvantage. On the other hand, in a column, the effluent concentration remains close to zero until the column is mostly saturated, at which point the effluent concentration rapidly increases. In certain applications this can be a disadvantage over well-mixed systems.

It is desirable in some cases to provide a system that has attributes of a well-mixed sorbent suspension and attributes of an adsorbent column, referred to herein as a "two-stage adsorbent system." For example, in a complex system involving many adsorbable substances, it may be desirable to have a mode of operation having the advantages of both a well-mixed system and a column. This is particularly true where some of the adsorbable substances in a fluid stream are desirable and their removal should be minimized.

Figure 20:
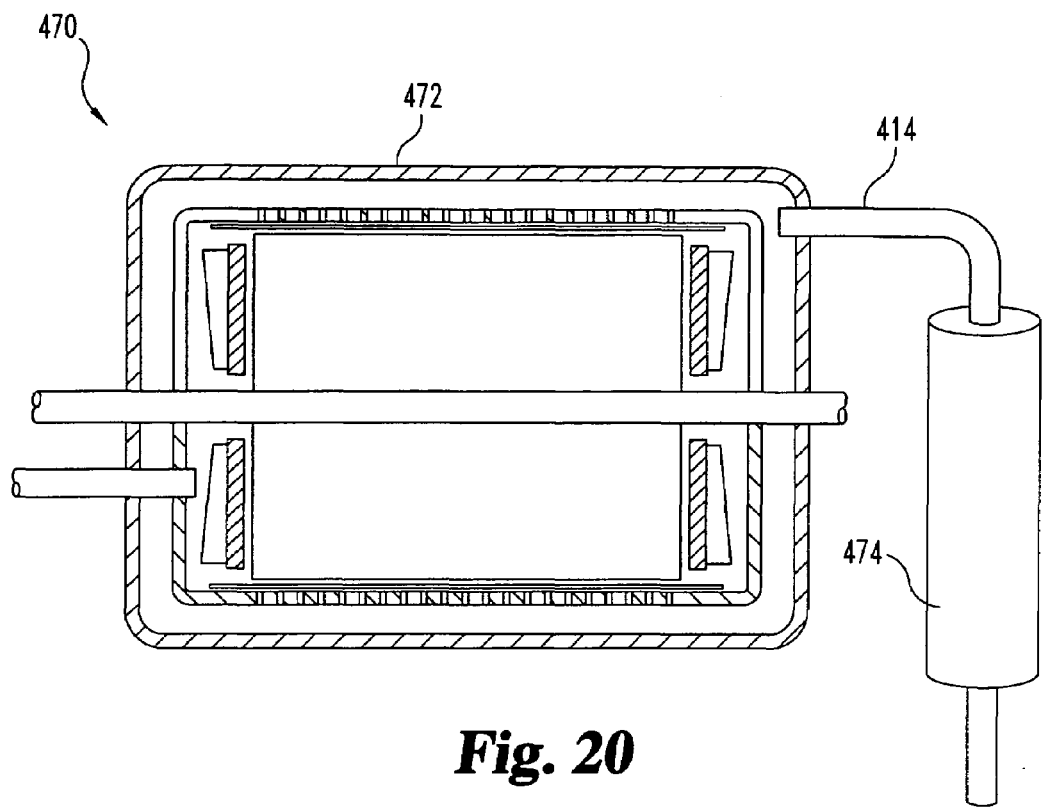
FIG. 20 is a partial cross-sectional view of yet another embodiment of a sorbent reactor in combination with a column supporting a solid adsorbent for use in the extracorporeal treatment of blood in accordance with the present invention.

FIG. 20 illustrates an embodiment of a two-stage adsorbent system 470 including a centrifugal reactor 472 and an adsorbent column 474 for the extracorporeal treatment of blood or other fluid in accordance with the present invention. Centrifugal reactor 472 can be configured substantially as has been described above for either of reactors 400 or 440. Consequently, the same reference numbers will be used to denote the same or like components. Outlet 414 can provide a fluid connection to a column 474 containing a solid adsorbent material. Consequently, the centrifugal reactor 472 is provided in series with the column-supported adsorbent 474. A wide variety of column designs and configurations that are available commercially can be used in connection with the present invention. However, it will be observed that the configuration of the column may significantly affect the flow rate of the treatment fluid through the system.

Figure 21:
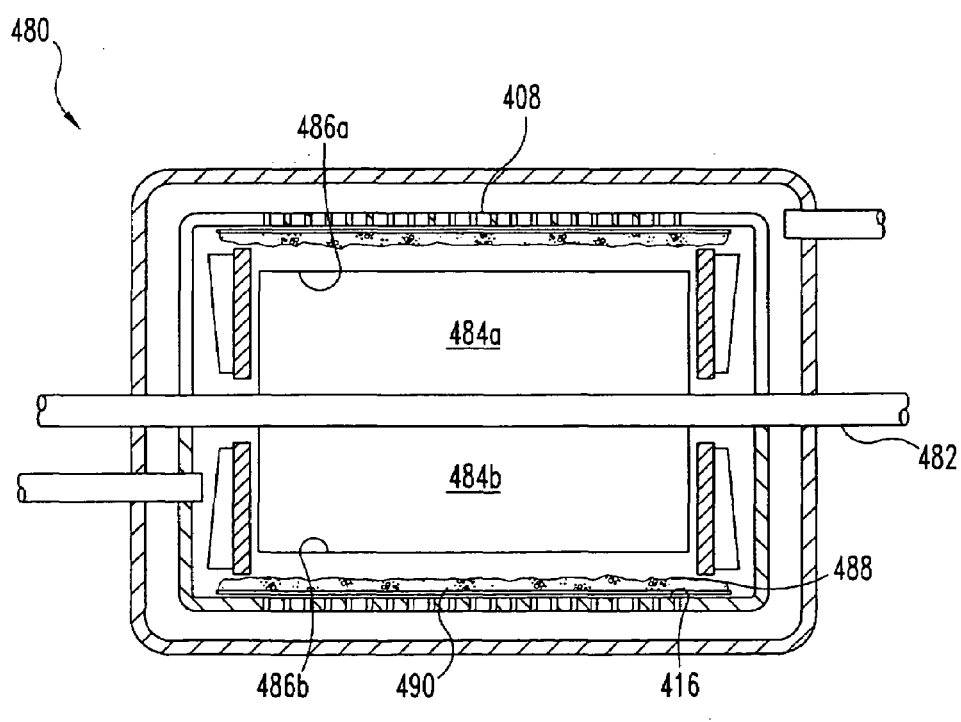
FIG. 21 is a cross-sectional view of another embodiment of a sorbent reactor having a rotor configured to allow the accumulation of a layer of sorbent particles at the membrane interface for use in the extracorporeal treatment of blood in accordance with the present invention.

In alternative two-stage adsorbent systems, both functionalities are provided in a single sorbent reactor by control of operating conditions of the reactor. In this regard, FIG. 21 provides another embodiment of a dual-stage centrifugal reactor 480 for the extracorporeal treatment of blood or other fluid in accordance with the present invention that provides similar functions to the reactor-column series described above as assembly 470. Reactor 480 can be provided substantially as has been described above for reactors 400 and 440. Consequently, the same reference numbers will be used to describe the like or same components. Notably, reactor 480 includes a rotor 482 having a plurality of paddles 484a and 484b. In this embodiment, paddles 484a and 484b do not extend all the way to the sidewall portion 408. Rather, paddles 484a and 484b are truncated, allowing a greater gap 488 between edges 486a, 486b of the respective paddles 484a, 484b and membrane 416. As a result of this gap, solid adsorbent particles 490 can accumulate in gap 488 against membrane 416. This accumulation of particles, in effect, provides a layer of stationary adsorbent that functions as a short column of solid adsorbent material deposited on the inner surface of membrane 416, which provides an alternative two-stage assembly design. When the effluent concentration must be minimized, this dual mode provides a mechanism to do so within certain limits.

Another advantage of using a sorbent suspension reactor in accordance with the invention to provide a two-stage adsorbent system is that the deposited sorbent layer can be dynamically deposited, re-suspended and optionally re-deposited, multiple times if desired to achieve a given adsorption level or profile. For example, it is possible, once the reactor has operated for some time in dual mode, to then speed up the rotor and remove the deposited adsorbent layer. Since the system is well mixed, a new equilibrium will be established, perhaps reducing the average saturation level of the particles in suspension. This technique would be particularly advantageous in some adsorbent systems, for example, systems featuring binding curves that are highly non-linear and non-monotonic. In addition, it is also possible to create a layer dynamically, where previously in the process, no layer was present.

In practice, many applications will involve not constant, but varying influent substance concentrations. In the case of extracorporeal blood treatments, for example, the influent concentration will decline over time. In such situations, dynamic modification of the reaction kinetics may prove especially helpful.

Figure 22:
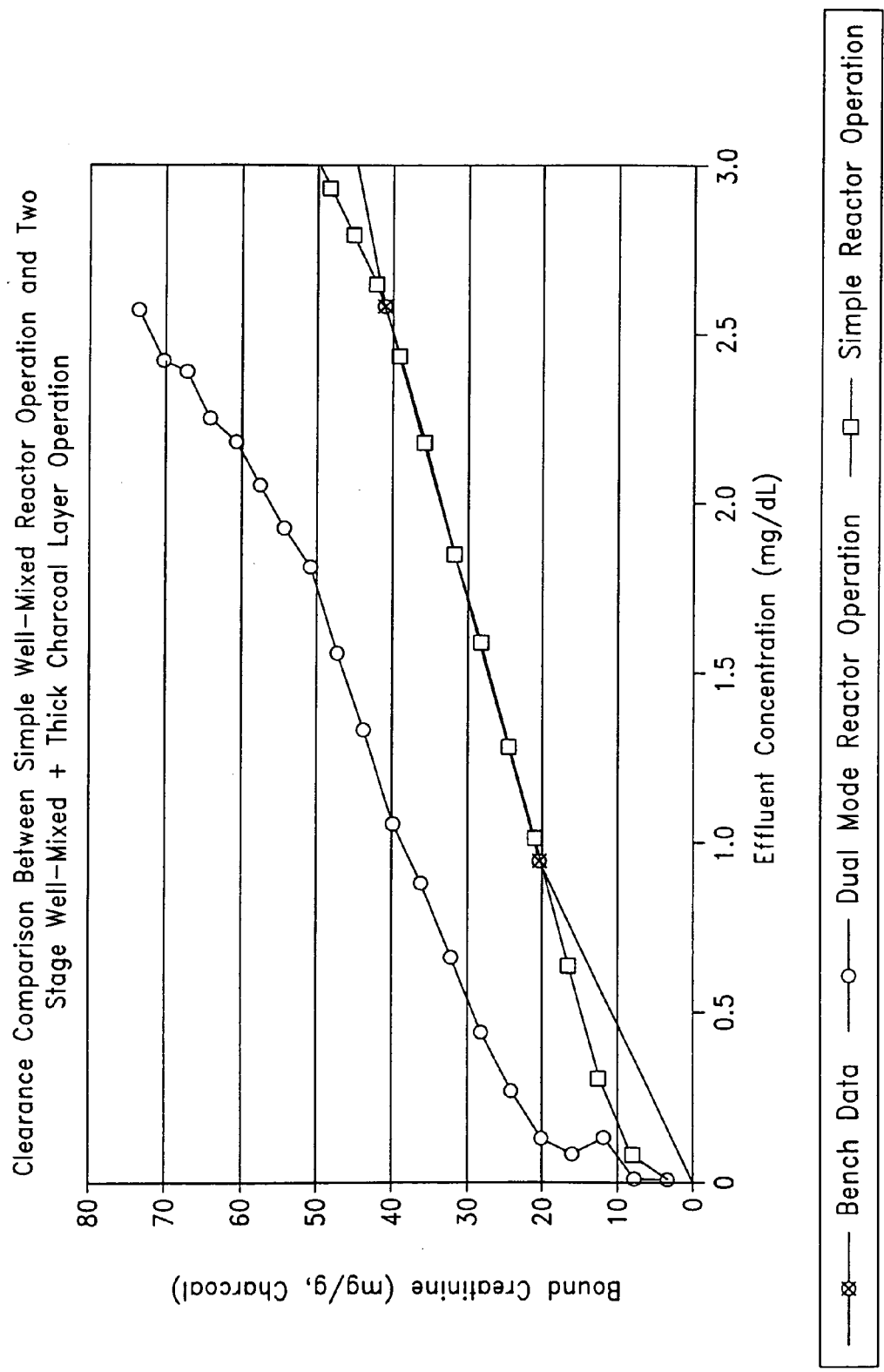
FIG. 22 is a graph comparing the ability of a dual-stage centrifugal reactor to bind creatinine compared to a "well-mixed" centrifugal reactor as a function of effluent concentration.
Figure 23:
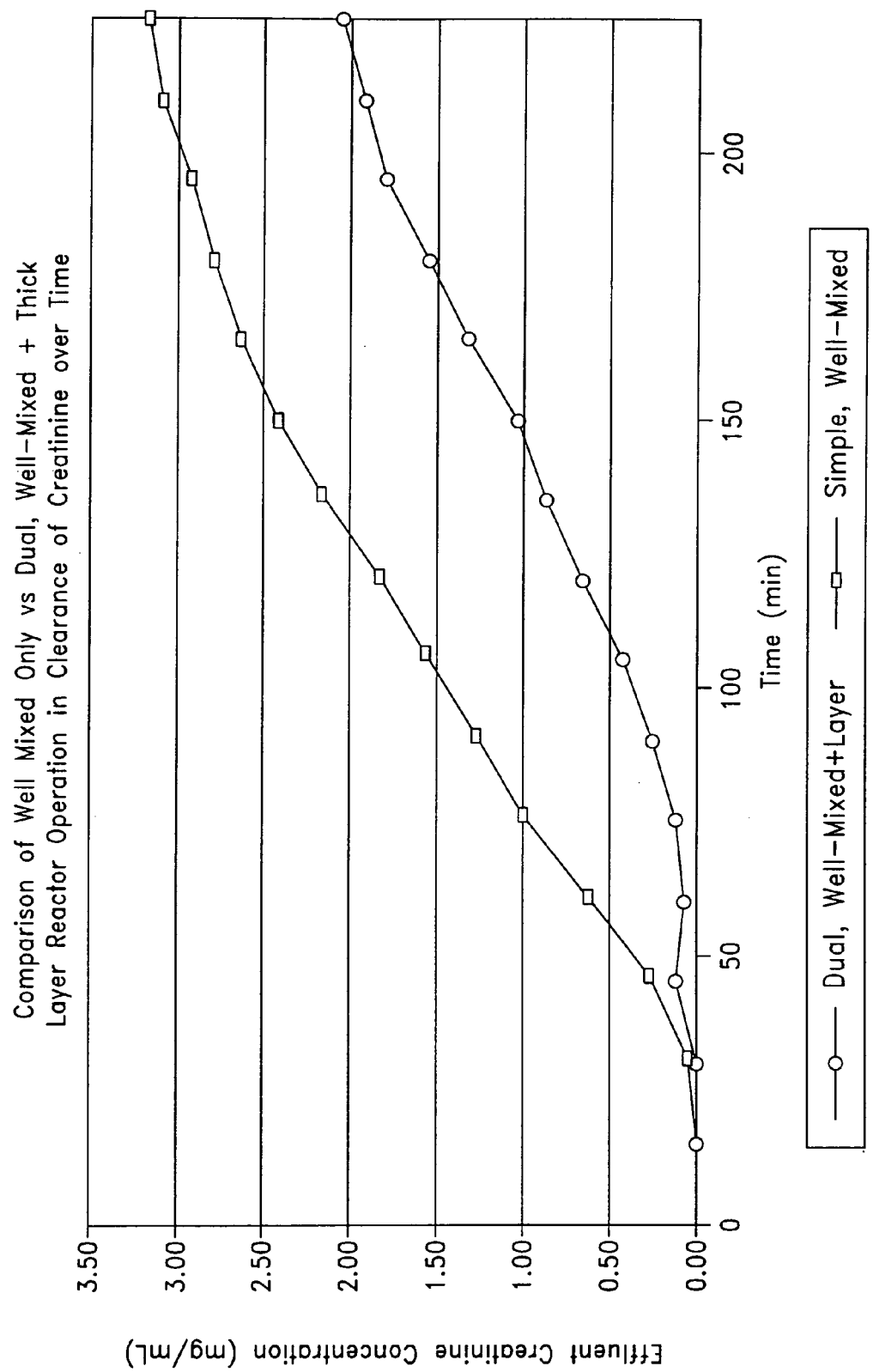
FIG. 23 is a graph comparing the performance of a dual-stage centrifugal reactor to remove creatinine compared to a "well-mixed" centrifugal reactor as a function of time.

FIG. 23 is a graph comparing the performance of a well-mixed reactor, such as, for example, reactors 400 and/or 440, to the performance of a dual-stage centrifugal reactor as illustrated in reactor 480. The data set forth in FIG. 22 compares the efficiency of each system in removing creatinine from a normal saline solution. The data are from a reactor whose basic construction is essentially as shown in Figure 480. The only difference between the simple reactor operation and the dual-mode reactor operation is in rotor speed. All other variables were controlled to be the same. In the simple reactor operation, rotor speed was high in order to preclude significant accumulation of sorbent on the filter membrane. In the dual-mode operation, rotor speed was much reduced in order to allow a "short packed column" to form on the filter membrane. The graph may be interpreted as follows: Note that the simple operation followed bench data closely. Bench data were obtained by using known amounts of substances in a stir-bar mixed beaker of charcoal suspension. For any point on the "Effluent Concentration" axis, note that the amount of creatinine (toxin) that was bound by the sorbent (hence removed from the blood stream of a theoretical patient) is greater for the dual-mode system than for the simple system. It can be observed from the graph that the dual-stage centrifugal reactor provides better performance to bind creatinine in the saline carrier medium.

FIG. 23, from the experiment of FIG. 22, is another graph comparing the well-mixed reactor with that of the dual-stage centrifugal reactor comparing the ability of each system to remove creatinine from the saline over time. It can be observed from the graph that the dual-stage centrifugal reactor provides greater clearance or removal of the creatinine and at a higher rate than that of the well-mixed reactor. At any point in time, the effluent concentration of creatinine (which, in a working system, would be re-entering the blood steam of a patient), is lower for the dual-mode system, than for the simple system.

The sorbent suspension provided in the sorbent reactors 50, 90, 200, 400, 440, 470, and 480 illustrated and described herein can include a wide variety of components. Examples of suitable sorbent suspensions are described in U.S. Pat. Nos. 5,277,820; 5,919,369; and 6,348,162, which are incorporated by reference herein in their entity. The solid component can include a powdered surface adsorptive agent. For example, for plasmafiltration or hemofiltration, the solid component can be any one of many known to those practiced in this area but is preferably powdered activated charcoal. Further, the powdered surface adsorptive agent preferably has an average particle diameter of not greater than about 100 microns. More preferably, this average particle diameter is less than about 50 microns, with 90 weight percent (wt %) or more of the particles having diameters not greater than about 75 microns. Particles exceeding 75 microns in diameter can be screened if necessary. Most preferably, the powdered charcoal used in plasmafiltration and hemofiltration in accordance with the invention has an average particle diameter of not greater than about 20 microns. As one example, a suitable finely powdered activated charcoal sold under the trade name Norit A Supra is available from American Norit Company, Inc. of Jacksonville, Fla., U.S.A., which has a mean (by weight) particle size of about 20 µm and can be screened to remove particles larger than those desired. Other suitable sorbents include without limitation: powdered silica, cation exchange resins, crystalline cation exchangers such as zeolites and zirconium silicate, anion exchange resins, sorbent particles with bound antibodies or antigens, and macromolecular compounds with toxin binding capacity.

One preferred sorbent suspension suitable for use in a sorbent suspension reactor provided by the present invention includes only charcoal and is free from ion-exchangers or macromolecular flow inducing agents. However, macromolecular flow inducing agents, when used, function to maintain the stability of the sorbent suspension formulation (i.e. helps to prevent solids from settling out of suspension) and maintain the flow properties of the suspension. One desirable flow-inducing agent is a nonionic, hydroxyl-containing polymer such as a glycol derivative. Suitable agents of this type are Pluronic™ polyols available from BASF Wyandotte of Parsippany, N.J., U.S.A. These Pluronic™ polyols are polyoxyalkylene derivatives of propylene glycol. Another flow agent that has been included in some suspensions is macroreticular polyvinylpyrrolidone.

The types and amounts of electrolytes included in the treatment fluid formulation will depend upon the specific needs of the patient and will be readily determinable by physicians or others skilled in the area. Typically, the electrolytes will include sodium and chloride (e.g. optionally provided as sodium chloride) and can also include bicarbonate, potassium, calcium, or any other electrolytes to be regulated in the patient. As indicated, however, the types and amounts of electrolytes may vary widely depending on patient needs.

The sorbent suspension formulation may also include an ion-exchanger to bind ionic chemicals, e.g., ammonium, which may occur in the patient's blood. Many suitable ion exchangers, including both resins and other materials such as zeolites, are known in the art. When included, the ion-exchanger is preferably a cation-exchange resin, which is desirably loaded with sodium or calcium. For example, to date, sodium polystyrene sulfonate has been a preferred material.

The surface adsorptive agent, electrolytes, flow inducing agents, and any other additives will usually comprise about 5% to 30% by weight of the initial sorbent suspension formulation as a whole, with the remainder being water. Typically, solid sorbents will comprise about 2% to 25% by weight of the initial suspension formulation, and electrolytes will comprise about 1% to 5% of the suspension formulation. Within these parameters, more preferred sorbent suspension formulations comprise about 2% to 20% powdered surface adsorptive agent, up to about 10% ion-exchanger, and up to about 1% flow agent such as a polyol and/or polyvinylpyrrolidone.

The sorbent suspension can also include viable hepatic cells, e.g. xenogenic or allogenic cells, alone or in combination with one or more of the solid adsorbents and other materials described above, to assist in the effective removal of toxins. For example, hepatocytes can be isolated from suitable donor tissue, purified, and microencapsulated in polymer. These microencapsulated cells can then be used directly in the sorbent suspension or can be cryopreserved until use. When hepatic cells are so used, plasma is effectively separated from the blood by passage through a plasmafilter membrane, and proteins and toxins are carried into contact with the cells in the sorbent reactor. After the cells have acted upon the toxins, the plasma is returned through the plasmafilter membrane and back into the patient.

As has been described above, the present invention can be used for a variety of treatments including extracorporeal blood treatments, treatment of drug overdose, detoxification of the plasma and/or blood, treatment of sepsis, and treatment of various immune diseases. Separation membranes in separation devices 23, 190 and/or filters in sorbent reactors 50, 90, 200, 400, 440, 470, and 480 can be varied to accommodate various treatment regimes. For example, separation device 23, 190 can include a plasma filter or any filter used in renal replacement therapy, preferably a hollow fiber filter. Additionally, the treatment fluid composition can be varied for the various regimes. Additional components such as various electrolytes, nutrients, sugars, albumin, and/or antibiotics can be added to the treatment fluid to ensure expedient medical treatment of the patient.

Furthermore, the sorbent reactors 50, 90, 200, 400, 440, 470, and 480 and the extracorporeal blood treatment systems 10 and 180 illustrated and described herein are compatible with a wide variety of commercially-available dialysis or treatment components. In preferred embodiments, the reactors 50, 90, 200, 400, 440, 470, and 480 can be readily included in existing commercial extracorporeal blood treatment systems and/or replace the existing reactors used in those systems. Examples of these commercial products include BioLogic-DT and BioLogic-PF System, (by HemoCleanse, Inc.), MARS (Molecular Adsorbent Recirculating System by Teraklin), ELAD® (Extracorporeal Liver Assist Device by Vital Therapies, Inc.), LiveRx 2000 (by Excorp Algenix, Inc.), Sybiol (by MultiCell Technologies, Inc.), and HepatAssist (by Circe Biomedical, Inc.).

The invention also finds advantageous use in peritoneal dialysis systems for conditioning a peritoneal dialysate fluid for recycling into the peritoneal cavity of the patient. In one embodiment of the invention, a peritoneal dialysis system includes a treatment fluid circuit including a conduit for passing treatment fluid to a patient's peritoneal cavity and a conduit for passing treatment fluid out of the patient's peritoneal cavity. The treatment fluid circuit also includes a sorbent reactor made or selected in accordance with the invention that includes an inlet line in fluid communication with the conduit that passes treatment fluid out of the patient's peritoneal cavity, and an outlet line in fluid communication with the conduit that passes the treatment fluid into the patient's peritoneal cavity. The sorbent reactor can have the same features as that described above in connection with an extracorporeal blood treatment system. Thus, to use an inventive sorbent reactor in connection with peritoneal dialysis, a treatment fluid is introduced into a patient's peritoneal cavity and recovered from the peritoneal cavity. It is then passed through a sorbent reactor and then reintroduced into the peritoneal cavity.

The invention relates to the use of a sorbent suspension for toxin removal by placement of the sorbent into a reactor through which treatment fluids can flow after they leave a separation device, such as, for example, a dialyzer, a hemofilter, or a plasmafilter. A filter in the device withholds sorbent particles while letting the treatment fluid pass. In a treatment system in which the treatment fluid includes proteins, it is important that the filter have pore sizes large enough to pass the proteins. The treatment fluid can then return to contact with the membranes of a dialyzer, hemofilter, or other separation membrane, or return directly to the blood in the case of plasma leaving a plasmafilter. The sorbent suspension reactors (SSR) as described herein can be used as an "add on" processor for dialysate or ultrafiltrate on standard dialysis or hemofiltration machines, or for plasma as an add-on to plasma separating machines.

The present invention contemplates various modifications as would occur to those skilled in the art. It is also contemplated that treatment processes embodied in the present invention can be altered, combined, or added to other treatment processes as would occur to those skilled in the art without departing from the spirit of the present invention. In addition, while various embodiments of blood treatment systems, components of these systems and sorbent reactors have been described with specific features and characteristics, it will be understood that the different features and characteristics of one embodiment of the systems, components or reactors can be combined with another embodiment or substituted for a feature or characteristic of another embodiment. All publications, patents, and patent applications cited in this specification are herein incorporated by reference as if each individual publication, patent, or patent application was specifically and individually indicated to be incorporated by reference and set forth in its entirety herein.

Further, any theory of operation, proof, or finding stated herein is meant to further enhance understanding of the present invention and is not intended to make the scope of the present invention dependent upon such theory, proof, or finding.

While the invention has been illustrated and described in detail in the drawings and foregoing description, the same is considered to be illustrative and not restrictive in character, it is understood that only the preferred embodiments have been shown and described and that all changes and modifications that come within the spirit of the invention are desired to be protected.

What is claimed is:

1. An extracorporeal treatment system comprising:
 a blood circuit including a first conduit for passing blood or other body fluid to a separation unit and a second conduit for passing the blood or other body fluid back to a patient, wherein the separation unit is configured to separate one or more components from the blood or body fluid into a treatment fluid; and
 a treatment fluid circuit comprising, in series, an inflow line for passing the treatment fluid from the separation unit to a sorbent reactor and an outflow line for passing the treatment fluid from the sorbent reactor to the separation unit or to the second conduit;
 wherein the sorbent reactor includes a housing including a first endwall portion, an opposite second endwall portion and cylindrical sidewall therebetween and defining an interior chamber configured to contain a liquid, a filter disposed in the interior chamber and partitioning the interior chamber into a first region and a second region, a sorbent suspension disposed in the first region, a first partition positioned in the inner region adjacent the first endwall portion to define a first shunt chamber between the first partition and the first endwall portion, a second partition positioned in the inner region adjacent the second endwall portion to define a second shunt chamber between the second partition and the second endwall portion and a rotor rotatably positioned in the first region;
 wherein the inflow line is positioned to pass the treatment fluid into the first region; and
 wherein the outflow line is positioned to pass the treatment fluid, after passage of the treatment fluid through the filter, from the second region to the separation unit or to the second conduit.

2. The system of claim 1 wherein the inlet is configured to pass the treatment fluid into the first region through an inlet filter.

3. The system of claim 1 wherein the separation unit comprises a dialyzer.

4. The system of claim 1 wherein the separation unit is a hollow fiber membrane.

5. The system of claim 1 wherein the separation unit comprises a plasma filtration device.

6. The system of claim 1 wherein the sorbent reactor includes a magnetic drive operable to rotate the rotor.

7. The system of claim 1 wherein the sidewall includes a plurality of holes to allow passage of the treatment fluid to the outflow line.

8. The system of claim 1 wherein the treatment fluid comprises plasma.

9. The system of claim 1 wherein the treatment fluid comprises a dialysate.

10. The system of claim 1, wherein the rotor is operable to move at least one paddle along a surface of the filter.

11. A body fluid treatment system comprising:
a first circuit for circulating a body fluid of a patient,
a second conduit including a treatment fluid flowing through a first conduit to a sorbent reactor, and a second conduit leading from the reactor; and
a separation membrane separating the first circuit from the second circuit, said membrane selected to allow a component of the body fluid to transfer therethrough to the second circuit;
wherein the sorbent reactor includes a housing including a first endwall portion, an opposite second endwall portion and cylindrical sidewall therebetween and defining an interior chamber configured to contain the treatment fluid, a filter disposed in the interior chamber and partitioning the interior chamber into a first region and a second region, a sorbent suspension disposed in the first region, a first partition positioned in the inner region adjacent the first endwall portion to define a first shunt chamber between the first partition and the first endwall portion, a second partition positioned in the inner region adjacent the second endwall portion to define a second shunt chamber between the second partition and the second endwall portion and a rotor rotatably positioned in the first region;
wherein the first conduit is positioned to pass the treatment fluid into the first region; and
wherein the second conduit is positioned to pass the treatment fluid, after passage of the treatment fluid through the filter, from the second region.

12. The system of claim 11 wherein body fluid comprises blood.

13. The system of claim 11 wherein the separation membrane is a hollow fiber membrane, hemofiltration membrane, plasma filtration membrane, or a dialyzer membrane.

14. The system of claim 11 wherein the second circuit includes a degasser.

15. The system of claim 11 wherein the treatment fluid flows through the reactor in a first direction.

16. The system of claim 15 wherein the first conduit and the second conduit are configured to alternately allow the treatment fluid to flow through the reactor in a second direction opposite the first direction.

17. The system of claim 11 wherein the sorbent has an average particle size of less than about 100 microns.

18. The system of claim 11, further comprising a fluid removal line connected to the second circuit.

19. The system of claim 18, further comprising a pump to remove excess treatment fluid through the fluid removal line.

20. The system of claim 11, wherein the rotor is operable to move at least one paddle along a surface of the filter.

21. A method for the extracorporeal treatment of a body fluid or a portion thereof, comprising:
conveying a body fluid or a portion thereof to a separation device;
separating one or more body fluid components from the body fluid or the portion into a treatment fluid;
passing the treatment fluid through a sorbent reactor to treat the treatment fluid; and
reintroducing the components into the body fluid;
wherein the sorbent reactor includes a housing including a first endwall portion, an opposite second endwall portion and cylindrical sidewall therebetween and defining an interior chamber, a filter disposed in the interior chamber and partitioning the interior chamber into a first region and a second region, a sorbent suspension disposed in the first region, a first partition positioned in the inner region adjacent the first endwall portion to define a first shunt chamber between the first partition and the first endwall portion, a second partition positioned in the inner region adjacent the second endwall portion to define a second shunt chamber between the second partition and the second endwall portion and a rotor rotatably positioned in the first region;
wherein the treatment fluid passes into the sorbent reactor through an inlet configured to pass the treatment fluid into the first region; and
wherein the treatment fluid passes out of the sorbent reactor through an outlet configured to pass the treatment fluid, after passage of the treatment fluid through the filter, out of the second region.

22. The method of claim 19 wherein the inlet is configured to pass the treatment fluid into the first region through an inlet filter.

23. An apparatus for passing a treatment fluid in contact with a sorbent suspension to condition the treatment fluid, said apparatus comprising:
a housing including a first endwall portion, an opposite second endwall portion and cylindrical perforated sidewall therebetween and defining an interior chamber configured to contain a liquid, said housing having an inlet and an outlet;
a filter disposed within said housing and partitioning said interior chamber into an inner region and an outer region;
a sorbent suspension and a treatment fluid contained within said inner region;
a first partition positioned in the inner region adjacent the first endwall portion to define a first shunt chamber between the first partition and the first endwall portion;
a second partition positioned in the inner region adjacent the second endwall portion to define a second shunt chamber between the second partition and the second endwall portion; and
a rotor rotatably mounted in said inner region, said rotor configured to mix the sorbent suspension and the treatment fluid and effective to apply a shear force parallel to the filter;
wherein said inlet is positioned to pass the treatment fluid into the inner region; wherein said outlet is positioned to pass the treatment fluid out of the outer region after passage of the treatment fluid through said filter;
wherein the treatment fluid is physiologically acceptable and compatible with blood; and wherein the filter features pore sizes of from about 0.1 microns to about 2 microns.

24. The apparatus of claim 23 further comprising an inlet filter and wherein the inlet is configured to pass the treatment fluid into the first region through said inlet filter.

25. The apparatus of claim 23 wherein the filter is a cylindrical filter.

26. The apparatus of claim 24 comprising a magnetic drive.

27. The apparatus of claim 26 wherein the filter is positioned on an inner surface of the perforated sidewall.

28. The apparatus of claim 23 wherein the first partition and the second partition each includes a plurality of vanes extending in a radial direction from the rotor.

29. The apparatus of claim 26 comprising a column containing an adsorbent therein and in fluid communication with the outlet to receive the treatment fluid.

30. The apparatus of claim 26 wherein the rotor comprises at least two blades extending radially therefrom.

31. The system of claim 23, wherein the rotor is operable to move at least one paddle along a surface of the filter.

32. The system of claim 23, wherein the rotor is operable to maintain the sorbent suspension in the treatment fluid in the inner region as the treatment fluid is passed through the filter.

33. The system of claim 23, wherein:
said filter extends about said inner region and along said inner region between opposite ends of said inner region; and
said rotor includes at least one elongated paddle extending along said filter between opposite ends of said inner region.

34. The system of claim 33, wherein said rotor includes a shaft extending between opposite ends of said inner region and said at least one paddle extends along and outwardly from said shaft.

35. A peritoneal dialysis system, comprising:
a treatment fluid circuit including a first conduit for passing treatment fluid to a patient's peritoneal cavity and a second conduit for passing treatment fluid out of the patient's peritoneal cavity; and
a sorbent reactor for treating the treatment fluid, the sorbent reactor including an inlet line in fluid communication with the second conduit and an outlet line in fluid communication with the first conduit;
wherein the sorbent reactor includes a housing including a first endwall portion, an opposite second endwall portion and cylindrical sidewall therebetween and defining an interior chamber, a filter disposed in the interior chamber and partitioning the interior chamber into a first region and a second region, a sorbent suspension disposed in the first region, a first partition positioned in the inner region adjacent the first endwall portion to define a first shunt chamber between the first partition and the first endwall portion, a second partition positioned in the inner region adjacent the second endwall portion to define a second shunt chamber between the second partition and the second endwall portion, and a rotor rotatably positioned in the interior chamber;
wherein the inlet is configured to pass the treatment fluid into the first region; and
wherein the outlet is configured to pass the treatment fluid, after passage of the treatment fluid through the filter, from the second region to the first conduit.

36. The system in accordance with claim 35 wherein the inlet is configured to pass the treatment fluid into the first region through an inlet filter.

37. The apparatus of claim 35 comprising a column containing a solid adsorbent therein and in fluid communication with the outlet to receive the treatment fluid.

38. A method for performing peritoneal dialysis, comprising:
introducing a treatment fluid into a patient's peritoneal cavity;
recovering the treatment fluid from the peritoneal cavity;
after said recovering, passing the treatment fluid through a sorbent reactor; and
after said passing, reintroducing the treatment fluid into the peritoneal cavity;
wherein the sorbent reactor includes a housing including a first endwall portion, an opposite second endwall portion and cylindrical sidewall therebetween and defining an interior chamber, a filter disposed in the interior chamber and partitioning the interior chamber into a first region and a second region, a sorbent suspension disposed in the first region, a first partition positioned in the inner region adjacent the first endwall portion to define a first shunt chamber between the first partition and the first endwall portion, a second partition positioned in the inner region adjacent the second endwall portion to define a second shunt chamber between the second partition and the second endwall portion, and a rotor rotatably positioned in the interior chamber;
wherein the treatment fluid passes into the sorbent reactor through an inlet configured to pass the treatment fluid into the first region; and
wherein the treatment fluid passes out of the sorbent reactor through an outlet configured to pass the treatment fluid, after passage of the treatment fluid through the filter, out of the second region.

39. The method in accordance with claim 38 wherein the inlet is configured to pass the treatment fluid into the first region through an inlet filter.

40. An apparatus for passing a treatment fluid in contact with a sorbent suspension to condition the treatment fluid, said apparatus comprising:
a housing including a first endwall portion, an opposite second endwall portion and cylindrical sidewall therebetween and defining an interior chamber configured to contain a liquid, said housing having an inlet and an outlet;
a filter disposed within said housing and partitioning said interior chamber into an inner region and an outer region;
a sorbent suspension contained within said inner region;
a first partition positioned in the inner region adjacent the first endwall portion to define a first shunt chamber between the first partition and the first endwall portion,
a second partition positioned in the inner region adjacent the second endwall portion to define a second shunt chamber between the second partition and the second endwall portion, and
a rotor rotatably mounted in said inner region, said rotor configured to urge the sorbent suspension through the first and second shunt chambers;
wherein said inlet is positioned to pass the treatment fluid into the inner region; and wherein said outlet is positioned to pass the treatment fluid out of the outer region after passage of the treatment fluid through said filter.

41. The apparatus of claim 40 wherein the inlet is configured to pass the treatment fluid into the first region through an inlet filter.

42. The apparatus of claim 40 comprising a magnetic drive operable to rotate the rotor within the inner region.

43. The apparatus of claim 40 wherein the filter is a cylindrical filter.

44. The apparatus of claim 40 wherein the first partition and the second partition each includes a plurality of vanes extending in a radial direction from the rotor.

45. The apparatus of claim 40 comprising a column containing an adsorbent therein and in fluid communication with the outlet to receive the treatment fluid.

46. The system of claim 40, wherein the rotor is operable to move at least one paddle along a surface of the filter.

* * * * *